United States Patent [19]
Sinackevich et al.

[11] Patent Number: 5,972,894
[45] Date of Patent: Oct. 26, 1999

[54] PEPTIDES HAVING POTASSIUM CHANNEL OPENER ACTIVITY

[75] Inventors: Nickolai V. Sinackevich; Alexi M. Rakhilov; Sergei V. Maslennikov, all of St. Petersburg, Russian Federation; Lawrence R. Green, Tacoma, Wash.

[73] Assignee: Cytran, Inc., Kirkland, Wash.

[21] Appl. No.: 08/908,328

[22] Filed: Aug. 7, 1997

[51] Int. Cl.$^6$ .................................................. A61K 38/00
[52] U.S. Cl. ............................................. 514/16; 514/19
[58] Field of Search ........................................ 514/16, 19

[56] References Cited

U.S. PATENT DOCUMENTS

| | | | |
|---|---|---|---|
| 4,057,636 | 11/1977 | Petersen | 424/263 |
| 4,200,640 | 4/1980 | Nagano et al. | 424/266 |

FOREIGN PATENT DOCUMENTS

| | | |
|---|---|---|
| 045 665 A1 | 2/1982 | European Pat. Off. . |
| 1417242 | of 1988 | U.S.S.R. . |
| 2007157 | of 1992 | U.S.S.R. . |
| 1807399 | of 1993 | U.S.S.R. . |

OTHER PUBLICATIONS

Friedel, Heather A., et al., "Pinacidil, A Review of its Pharmacodynamic and Pharmacokinetic Properties, and Therapeutic Potential in the Treatment of Hypertension," *Drugs, vol. 39*, (6) 1990, pp. 929–967.

Grover, Gary J., et al., "Cardioprotective Effects of the Potassium Channel Opener Cromakalim: Stereoselectivity and Effects on Myocardial Adenine Nucleotides," *J. Pharmac. & Expt'l. Therapeutics*, 257(1):156–162, 1991.

Lipton, Howard L., et al., "Pulmonary vasodilation to endothelin isopeptides in vivo is mediated by potassium channel activation," *J. Appl. Physiol.* 70(2):947–952, 1991.

Lynch, Jr., Joseph J., et al., "Therapeutic potential of modulating potassium currents in the diseased myocardium," Symposium "Therapeutic Potential of Modulating Potassium Currents in the Diseased Myocardium", Apr. 25, 1991.

Meisheri, Kaushik D., et al., "A Sensitive In Vitro Functional Assay to Detect $K^+$–Channel–Dependent Vasodilators," *J. Pharmac. Methods*, 24, 251–261 (1990).

Remington, Julianne, "Potassium Channel Implicated in Wide Array of Diseases," Press Release for Oregon Health Sciences University, (1996) http://www.orst.edu/Dept . . . nnect/con71/adelman.html.

Abele April et al., "Potassium Channel Activators Abolish Excitoxicity in Cultured Hippocampal Pyramidal Neurons," *Neuroscience Letters*, vol. 115, pp. 195–200, (1990).

Almquist R. G. et al., "Synthesis and Biological Activity of a Ketomethylene Analogue of a Tripeptide Inhibitor of Angiotensin Converting Enzyme" *J. Med. Chem.*, vol. 23, pp. 1392–1398, (1980).

Archives of Biochemistry and Biophysics, IUPAC–IUB Combined Commission on Biochemical Nomenclature; Abbreviations and Symbols for Chemical Names of Special Interest in Biological Chemistry; Revised Tentative Rules (1965), recommandations, vol. 115, pp. 1–12, (1966).

Ashford et al., Cloning and Functional Expression of a Rat Heart $K_{ATP}$ Channel, *Nature*, vol. 370, pp. 456–459, (Aug. 11, 1994).

Babenko A. P. et al., "Activation of ATP–Sensitive K+ Channels of Cardiomyocytes by Endogenous Cardiopeptides," *Bull. Eksp. Biol. Med.*, Russia, vol. 114, No. 7, pp. 54–56, (1992).

Ben–Ari et al., "Activators of ATP–Sensitive K+ Channels Reduce Anoxic Depolarization in CA3 Hippocampal Neurons," *Neuroscience*, vol. 37, pp. 55–60, (1990).

Carmeliet E., "Ion Channel Agonists: Expectations for Therapy," *Eur. Heart J.*, vol. 12, Supplement F, pp. 30–37, (1991).

Cook Nigel et al., "Anti–Vasoconstrictor Effects of the $K^+$ Channel Opener Cromakalim on the Rabbit Aorta–Comparison With The Calcium Antagonist Isradipine," *Br. J. Pharmacologie*, vol. 95, pp. 741–752, (1988).

Dilly S. G., "Cromakalim/Lemakalim, Experience in Hypertension and Nocturnal Asthma," *Conference Documentation, Potassium Channels '90*, The Royal College of Physicians, Dec. 6–7, 1990, 17 pages.

Downing S. J. et al., "Interaction Between Myometrial Relaxants and Oxytocin: a Comparison Between Relaxin, Cromakalim and Salbutamol," *J. Endocrinol.*, vol. 135, p. 29, (1992).

Evans B. E. et al., "Design of Nonpeptidal Ligands for a Peptide Receptor: Cholecystokinin Antagonists," *J. Med. Chem.*, vol. 30, pp. 1229–1239, (1987).

Escande et al., "K+ Channel Openers and 'Natural' Cardioprotection," *Trends in Pharm. Sci.*, vol. 23, pp. 269–272, (1992).

Fauchere, Jean–Luc, "Elements for the Rational Design of Peptide Drugs," *Adv. Drug. Res.*, vol. 15, pp. 29–69, (1986).

Gandolfo et al., "K+Channel Openers Decrease Seizures in Genetically Epiletic Rats," *Europ. J. Pharmac.*, vol. 167, pp. 181–183, (1989).

Gopalakrishnan Murali et al., "ATP–Sensitive K+ Channels: Pharmacologic Properties, Regulation, and Therapeutic Potential," in *Drug Dev. Res.*, vol. 28, pp. 95–127, (1993).

Grover Gary J. et al., "Anti–Ischemic Effects of the Potassium Channel Activators Pinacidil and Chromakalim and the Reversal of these Effects With the Potassium Channel Blocker Glyburide," *J. Pharmac. & Expt'l Therapeutics*, vol. 251, No. 1, pp. 98–104, (1989).

Grover Gary J. et al., "Reduction of Ischemic Damage in Isolated Rat Hearts by the Potassium Channel Opener, RP 52891," *Europ. J. Pharmac.*, vol. 191, pp. 11–18, (1990).

(List continued on next page.)

*Primary Examiner*—Theodore J. Criares
*Attorney, Agent, or Firm*—Townsend & Townsend and Crew LLP

[57] ABSTRACT

This invention concerns methods for prophylactic and therapeutic treatment of diseases responsive to the opening of potassium channels, peptides having potassium channel opener activities, and pharmaceutical compositions and kits comprising such peptides.

67 Claims, No Drawings

OTHER PUBLICATIONS

Grover Gary J. et al., "Cardioprotective Effects of the Potassium Channel Opener Cromakalim: Stereoselectivity and Effects on Myocardial Adenine Nucleotides," *J. Pharmac. & Expt'l Therapeutics*, vol. 257, No. 1, pp. 156–162, (1991).

Guermonprez J. L. et al., "A Double–Blind Comparison of the Long–Term Efficacity of a Potassium Channel Opener and a Calcium Antagonist in Stable Angina Pectoris," *Eur. Heart J.*, vol. 14, Supplement B, pp. 30–34, (1993).

Hann Michael M. et al., "On the Double Bond Isostere of the Peptide Bond: Preparation of an Enkephalin Analogue," *J. Chem. Soc. Perkin Trans.*, pp. 307–314, (1982).

Holladay M. W. et al., "Synthesis of Hydroxyethylene and Ketomethylene Dipeptide Isosteres," *Tetrahedron Lett.*, vol. 24, pp. 4401–4404, (1983).

Hudson, D. et al., "Methionine Enkephalin and Isosteric Analogues," *Int. J. Pept. Prot. Res.*, vol. 14, pp. 177–185, (1979).

Hruby V. J., "Conformational Restrictions of Biologically Active Peptides Via Amino Acid Side Chain Groups," *Life Science*, vol. 31, pp. 189–199, (1982).

Jennings–White Clive et al., "Synthesis of Ketomethylene Analogs of Dipeptides," *Tetrahedron Lett.*, vol. 23, No. 25, pp. 2533–2534, (1982).

Khlystov, V.V. et al., "Ultrastructure of the Periinfarction Zone in Experimental Myocardial Innfarction Treated With Cardiolin," *Archive Pathology*, (USSR) vol. 9, pp. 27–31, (1989).

Kidney et al., "Effect of an Oral Potassium Channel Activator, BRL 38227, on Airway Function and Responsiveness in Asthmatic Patients: Comparison With Oral Salbutamol," *Thorax*, vol. 48, pp. 130–133, (1993).

McPherson Grant A., "Current Trends in the Study of Potassium Channel Openers," *Gen. Pharmac.* vol. 24, No. 2, pp. 275–281, (1993).

Merrifield R. B., "Solid Phase Peptide Synthesis. I. The Synthesis of a Tetrapeptide," *J. Am. Chem. Soc.*, vol. 85, pp. 2149–2154, (1963).

Morley, J. S., "Modulation of the Action of Regulatory Peptides by Structural Modification," *Trends Pharm Sci.*, pp. 463–468, (Dec. 1980).

Nielsen–Kudsk Jens Erik et al., "Effects of Pinacidil on Guinea–Pig Airway Smooth Muscle Contracted by Asthma Mediators," *Europ. J. Pharmac.*, vol. 157, pp. 221–226, (1988).

Pavlenko V. S. et al., "Effect of a Polypeptide Preparation on the State of Myocardial Cell Energy Metabolism During Hypoxia and Ischemia," *Bull. Eksp. Biol. Med.*, (USSR), vol. 112, No. 7, pp. 24–27, (1991).

Pavlenko V. S. et al., "Effect of a Drug Isolated From the Heart on Biologic Energy of Cardiomyocytes in Hypoxia and Ischemia," *Patol. Fiziol. Eksp. Ter.*, (Russia), vol. 2, pp. 20–24, (1992).

Selye H. et al., "Simple Techniques for the Surgical Occlusion of Coronary Vessels in the Rat," *Angiology*, vol. 11, pp. 398–407, (1960).

Small R. C. et al., "Potassium Channel Opening Drugs and the Airways," *Brazilian J. Med. Biol. Res.*, vol. 25, No. 10, pp. 983–998, (1992).

Spatola, Arno F., "Peptide Backbone Modifications: a Structure–Activity Analysis of Peptides Containing Amide Bond Surrogates, Conformational Constraints," Chemistry and Biochemistry of Amino Acids, Peptides, and Proteins, vol. 7, Chapter 5, Editor Boris Weinstein, eds. 1983, pp. 267–357, (1983).

Spatola, A. F., "Structure–Activity Relationships of Enkephalins Containing Serially Replaced Thiomethylene Amide Bond Surrogates," *Life Science*, vol. 38, pp. 1243–1249, (1986).

Veber and Freidinger, "The Design of Metabolically–Stable Peptide Analogs," *TINS*, pp. 392–396, (Sep. 1985).

Woollard et al., "Inosine as a Selective Inotropic Agent on Ischaemic Myocardium," *Cardiovasc. Res.*, vol. 15, pp. 659–667, (1981).

CA: 68; 47156z, Schleifer et al., 1968.

CA: 79; 124120q; Goldman, 1973.

CA: 118; 81406s; Wipf et al., 1993.

PEPTIDES HAVING POTASSIUM CHANNEL OPENER ACTIVITY

FIELD OF THE INVENTION

This invention relates generally to methods for treating and preventing diseases responsive to opening of potassium channels, peptides having potassium channel opener activities, and pharmaceutical compositions and kits containing such peptides.

BACKGROUND OF THE INVENTION

Potassium ($K^+$) channels are important regulators of numerous biological processes, including secretory processes, muscle contraction, and post-ischemic cardioprotection. Electrophysiological studies have disclosed the existence of potassium channels in nearly all cell types. Gopalakrishnan et al., *Drug Dev. Res.* 28: 95–127 (1993). Such channels are present in various forms that are generally distinguishable by their respective structural, biophysical, and pharmacological characteristics. Id. It is generally well known that the opening of potassium channels in a electrically excitable cell having such channels results in an increased flow of potassium ions from inside the cell to outside the cell. This flow of potassium ions causes a measurable change in the resting membrane potential of the cell and leads to membrane hyperpolarization and relaxation of the cell. Activation of potassium channels stabilizes cell membrane potential and generally reduces cell excitability.

Potassium channels have been implicated in a large number of diseases, including cardiovascular disease, asthma, hypertension, Parkinson's disease, Alzheimer's disease, diabetes, epilepsy, high blood pressure, and feeding and appetite disorders. It is generally believed that the malfunctioning of these potassium channels or the existence of regulation defects in processes that activate such potassium channels may play a significant role in the pathogenesis of such diseases and illnesses. As a result, compounds that are of assistance in opening potassium channels and, consequently, in modulating electrophysiological functioning of the cells may have significant therapeutic and prophylactic potential for treating or alleviating such conditions.

Potassium channel opener compounds exhibit a diverse array of biological and pharmacological activities. Presently known potassium channel openers include cromakalim, pinacidil (U.S. Pat. No. 4,057,636), and nicorandil (U.S. Pat. No. 4,200,640). These compounds are believed to exert their effects primarily via the ATP-sensitive potassium channels. They have a high affinity for vascular smooth muscle cells and are characterized by their ability to relax vascular smooth muscle. Escande et al., *Trends in Pharm. Sci.* 23: 269–272 (1992). Cromakalim, for instance, has been observed to induce hyperpolarization of vascular smooth muscle tissue, relax vessels, and reduce the effects of ischemic damage on the myocardium. Grover et al., *J. Phaimac. & Expt'l Therapeutics* 257: 156–162 (1991). Cromakalin also appears to be an effective chemotherapeutic agent for cardiac dysrhythmias and irritable bowel, both of which are associated with potassium channel activation. In addition, cromakalim has been found to inhibit premature uterine contractions when used in combination with estrogen and relaxin. Downing et al., *J. Endocrinol.* 135: 29 (1992). Pinacidil has been shown to dilate precapillary vessels and relax smooth muscle. Nielsen-Kudsk et al., *Europ. J. Pharmac.* 157: 221–226 (1988). Cromakalim and pinacidil have been found to reduce the extent of myocardial ischemic injury. Grover et al., *J. Pharmac. & Expt'l Therapeutics* 251: 98–104 (1989). Certain potassium channel openers, including cromakalim, have been observed to act on tracheal smooth muscle cells and to produce anti-asthmatic effects. Dilly, "Cromakalim/lemakalim, Experience in Hypertension and Nocturnal Asthma" in Conference Documentation, Potassium Channels '90, The Royal College of Physicians, Dec. 6–7, 1990. See also Small et al., *Braz. J. Med. Biol. Res.* 25(10): 983–998. This action is associated with membrane hyperpolarization towards the potassium equilibrium potential and with the promotion of the efflux of potassium ions from the muscle cells. Id. Furthermore, some potassium channel openers have been found to hyperpolarize neuronal cells and to possess anti-epileptic and anticonvulsant effects. See, e.g., Gandolfo et al., *Europ. J. Pharmac.* 167: 181–83 (1989); Abele et al., *Neuroscience Letters* 115: 195–200 (1990).

Unfortunately, presently known potassium channel openers typically produce serious side effects (including severe headaches, fluid retention, and reflex tachycardia) in subjects to whom they are administered. Additionally, many of the known potassium channel openers are unstable and their pharmacological effects are variable and difficult to reproduce. Kidney et al., *Thorax* 48: 130–133 (1993). Consequently, the therapeutic and prophylactic use of presently known potassium channel openers is limited.

A need exists for compounds having potassium channel opener activity that exert their respective therapeutic and prophylactic effects with little or no toxic side effects. The present invention fulfills this and other needs.

SUMMARY OF THE INVENTION

The present invention provides methods for the prophylactic or therapeutic treatment of diseases responsive to opening of potassium channels in a subject in need thereof. Such methods comprise administering to a subject in need thereof an effective amount of a peptide of the invention. The peptides of the invention include L-Glycyl-L-Glutamic acid (L-Gly-L-Glu), L-Valine-L-Threonine (L-Val-L-Thr), polymers of L-Gly-L-Glu and L-Val-L-Thr comprising no more than 16 amino acid residues and combinations thereof, and pharmaceutically acceptable salts thereof. The preferred peptides of the invention include L-Gly-L-Glu and L-Val-L-Thr. The methods of the invention are useful for the prophylactic or therapeutic treatment of a variety of diseases that are responsive to and sensitive to potassium channel activating properties.

In another aspect of the invention, methods are provided for the prophylactic or therapeutic treatment of cardiovascular diseases in subjects in need thereof. Such methods comprise administering to a subject an effective amount of a peptide of the invention as described above.

The invention also provides methods of inducing relaxation of smooth muscle in subjects in need thereof. Such methods comprise administering to the subject an effective amount of a peptide of the invention as described above.

In another aspect, methods of inducing relaxation of skeletal muscle in subjects in need thereof are provided. These methods comprise administering to the subject an effective amount of a peptide of the invention as described above.

Also provided are methods for the prophylactic or therapeutic treatment of diseases responsive to opening of potassium channels which comprise administering to a subject in need thereof an effective amount of a peptide that comprises a serial array of no more than about 16 L-amino acids, is extractable from myocardium in an acidic extract and isolatable therefrom in an included-volume of a G-25 superfine chromatographic resin, and has no effect on a tonic contraction of a smooth muscle specimen sample induced by a high potassium chloride concentration. In these methods, the potassium channel opener activity comprises a n increased flow of potassium ions from inside an electrically excitable cell to outside the cell via a membrane of the cell that has at least one potassium channel.

The invention also provide s pharmaceutical compositions in unit dosage form comprising per unit dosage a pharmaceutically acceptable carrier and a range of from about 0.01 milligram (mg) to about 1000 mg of L-Gly-L-Glu or L-Val-L-Thr or a pharmaceutically acceptable salt thereof. In a preferred aspect, the invention provides pharmaceutical compositions in unit dosage form comprising per unit dosage a pharmaceutically acceptable carrier and a range of from about 1 mg to about 100 mg of L-Gly-L-Glu, L-Val-L-Thr, or a pharmaceutically acceptable salt thereof.

In another aspect, the invention provides peptide polymers comprising at least two dipeptides, wherein each said dipeptide of said polymer is L-Gly-L-Glu or L-Val-L-Thr.

In yet another aspect of the invention, methods of preserving living tissues or organs are provided. These methods comprise contacting the tissue or organ with a composition comprising a pharmaceutically acceptable carrier and an effective amount of a peptide, wherein the peptide is L-Gly-L-Glu or L-Val-L-Thr or a pharmaceutically acceptable salt thereof.

The invention also provides kits for preserving living tissues or organs. Such kits include an effective amount of a peptide, wherein the peptide is L-Gly-L-Glu or L-Val-L-Thr or a pharmaceutically acceptable salt thereof.

DETAILED DESCRIPTION OF THE PREFERRED INVENTION

I. DEFINITIONS

Unless defined other wise, all technical and scientific terms used herein have the same meaning as commonly understood by those of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). As used herein, the following terms have the meanings ascribed to them unless specified otherwise. Although any methods and materials similar or equivalent to those described herein may be used in the practice or testing of the present invention, the preferred methods and materials are described. For purposes of the present invention, the following terms are defined below.

The terms "myocardial" and "myocardium" refer to the muscular layer of the heart, which includes muscle tissue, intraorgan vessels with their associated vascular smooth muscle, the neural transmission system of the heart, and interstices.

The term "myocardial peptide" means a peptide comprising a serial array of no more than about 16 L-amino acid residues in length, which is extractable from myocardium in an acidic extract and is isolatable therefrom in an included-volume of a G-25 superfine chromatographic resin, and which has no effect on a tonic contraction of a smooth muscle specimen sample induced by a high potassium chloride concentration.

The terms "potassium channel opener" and "potassium channel opener activity" refer generally to an increased flow of potassium ions from inside an electrically excitable cell to outside the cell via a membrane of the cell which has at least one potassium channel. Potassium channel opener activity may be observed by measuring an increase in the flow of potassium ions from inside a cell to outside the cell via a potassium channel in the cell membrane.

The term "cardiovascular disease" generally means diseases and pathological conditions relating to or involving the heart or blood vessels. Examples of cardiovascular diseases include all forms of ischemic heart disease, cardiac dysrhythmia and cardiac arrhythmia, congestive heart failure, and hypertensive disease listed in *International Classification of Diseases*, Vol. 9, *Clinical Modification, Easy Coder* (1997) ("ICD 9 CM") (incorporated herein by reference in its entirety for all purposes), as well as all cardiovascular diseases responsive or sensitive to vasodilation, and all cardiovascular diseases described in E. Braunwald, HEART DISEASE: A TEXTBOOK OF CARDIOVASCULAR MEDICINE (3d ed. 1988) (incorporated herein by reference in its entirety for all purposes).

The term "pharmaceutically acceptable salt" refers to non-toxic acid addition salts, including salts formed with inorganic acids, such as hydrochloric acid, hydrobromic acid, phosphoric acid, sulfuric acid and perchloric acid, and salts formed with organic acids, such as acetic acid, oxalic acid, maleic acid, malic acid, tartaric acid, citric acid, succinic acid or malonic acid. Other pharmaceutically acceptable salts include inorganic nitrate, sulfate, acetate, malate, formate, lactate, tartrate, succinate, citrate, p-toluenesulfonate, and the like, including, but not limited to, cations based on the alkali and alkaline earth metals, such as sodium, lithium, potassium, calcium, magnesium and the like, as well as non-toxic ammonium, quaternary ammonium, and amine cations, including, but not limited to, ammonium, tetramethylammonium, tetraethylammonium, methylamine, dimethylamine, trimethylamine, triethylamine, ethylamine, and the like.

The term "pharmaceutical composition" means a composition suitable for pharmaceutical use in a subject, including an animal or human. A pharmaceutical composition generally comprises an effective amount of an active agent and a pharmaceutically acceptable carrier.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result. The desired result may comprise a subjective or objective improvement in the recipient of the dosage.

A "prophylactic treatment" is a treatment administered to a subject who does not exhibit signs of a disease or exhibits only early signs of a disease, wherein treatment is administered for the purpose of decreasing the risk of developing pathology.

A "therapeutic treatment" is a treatment administered to a subject who exhibits signs of pathology, wherein treatment is administered for the purpose of diminishing or eliminating those pathological signs.

The term "organ" means body systems such as the heart, liver, lung, kidney, brain, adrenal, vascular-endothelial system, immune system, and the like.

The term "subject" is intended to mean an animal, such as a mammal, including a human. Non-human animals subject to treatment include, for example, fish, birds, and mammals such as cows, sheep, pigs, horses, dogs and cats.

The term "disease responsive to opening of potassium channels" means a pathological condition, disease, or disorder that is prophylactically or therapeutically responsive to, sensitive to, or associated with the activation or opening of potassium channels in cells of the target tissue.

The term "hypoxia" refers to a pathological condition resulting from a deficiency in the amount of oxygen reaching bodily tissues.

The term "anoxia" refers to a pathological condition resulting from an absence of oxygen.

II. PEPTIDES OF THE INVENTION

A. General Characteristics and Uses

The present invention provides a novel class of regulatory peptides that are distinguished by their ability to treat or prevent diseases responsive or sensitive to the opening of potassium channels, or associated with potassium channel activation. As noted above, potassium channels are present in nearly all cell types, including myocardial cells, smooth muscle cells, skeletal muscle cells, pancreatic beta cells, secretory cells, neural cells, cells of the brain, and the like, and are involved in the proper functioning of most cells. The mechanism of action of the peptides of the invention is believed to involve the activation of the potassium channels located in the membranes of such cells.

The subject peptides generally exhibit the biological and pharmacological activities of known potassium channel opener compounds and thus are useful in treating diseases frequently treated by known potassium channel openers. For example, the peptides of the invention share the common property of inducing relaxation of smooth muscle, a characteristic feature of known potassium channel openers. These peptides reduce and inhibit the contractile activity of a variety of smooth muscle tissues, including intestinal, vascular, tracheal, bronchial, and uterine smooth muscle. As a result, the peptides of the invention are useful in treating and preventing disorders that may be alleviated or prevented by the relaxation of smooth muscle. For instance, since the subject peptides relax intestinal smooth muscle, they are useful in treating and preventing hyper-reactive disorders of the intestine, such as irritable bowel.

Because they relax vascular smooth muscle, the subject peptides also induce vasodilation, as do known potassium channel openers. See, e.g., Guermonprez et al., *Eur. Heart J.*: 14 (Suppl. B): 30–34 (1993). Vasodilation typically produces an increase in the volume of blood flowing through a vessel and/or decrease blood pressure in the vessel. With their vasodilating effects, the subject peptides are useful in the prophylactic and therapeutic treatment of diseases that responsive or sensitive to vasodilation, such as those that may be treated by decreasing blood pressure in vessels or increasing the volume of blood flowing through vessels. For example, the subject peptides are useful in treating and preventing hypertension, which is characterized by abnormally high arterial blood pressure, because they promote vasodilation and reduce blood pressure. Similarly, because they improve blood flow, the subject peptides are useful in treating and preventing angina pectoris, a severe paroxysmal pain in the chest associated with an insufficient supply of blood to the heart.

The peptides of the invention also exhibit anti-ischemic and cardioprotective properties typically observed with known potassium channel openers and thus serve as useful anti-ischemic and cardioprotective agents. It is generally known that potassium channels are present in cardiac cells and that activation of such channels results in membrane hyperpolarization and shortening of action potential duration. See, e.g., Gopalakrishnan et al., supra; Grover et al., *Europ. J. Pharmac.* 191: 11–18 (1990); Grover et al., *J. Pharnac. & Expt'l Therapeutics* 251: 98–104 (1989); Grover et al., *J. Phannac. & Expt'l Therapeutics* 257: 156–162 (1991). Known potassium channel openers have been shown to reduce myocardial ischemia and protect against ischemia (i.e., to exert cardioprotective effects). See, e.g., Guermonprez, supra. It is believed that the activation of potassium channels in cardiac tissue by potassium channel openers reduces or reverses ischemia-induced depolarization and reperfusion damage, possibly via membrane hyperpolarization (i.e., increasing the resting potential of cells toward preischemic levels) and a reduction in cellular calcium ion influx. Grover et al., *J. Pharmac. & Expt'l Therapeutics* 251: 98–104 (1989); Grover et al., *J. Pharmac. & Expt'l Therapeutics* 257: 156–162 (1991).

In the present invention, the subject peptides significantly reduce the effects of ischemic damage in myocardial tissue, restore cardiac muscle contractility following ischemia, and safeguard and protect myocardial tissue from further damage due to ischemia. The subject peptides also act as anti-arrhythmic agents. Given these activities, which are observed in known potassium channel openers, the peptides of the invention are useful in treating and preventing a variety of cardiovascular diseases responsive to potassium channel activation, including ischemic heart disease, cardiac arrhythmias, congestive heart failure, stroke, and angina pectoris. See, e.g., Guermonprez, supra.

The subject peptides also relax airway smooth muscle (e.g., tracheal smooth muscle) and exhibit bronchodilatory effects (i.e., increasing caliber of bronchus or bronchial tube), as do known potassium channel opening drugs. Thus, they are beneficial in treating and alleviating certain tracheal and bronchial disorders, including bronchial asthma, bronchospastic diseases, and bronchospastic syndrome. See, e.g., Small et al., *Braz. J. Med. Biol. Res.* 25(10): 983–998.

Additionally, the peptides of the invention are beneficial in treating and preventing diseases of the brain that are associated with potassium channel activation. Known potassium channel openers have been found to activate potassium channels in brain cells, thereby reducing neuronal excitability of such cells and producing anticonvulsant effects on such cells. Correspondingly, the subject peptides are expected to be useful in treating and preventing neurodegenerative diseases associated with or responsive to potassium channel activation and/or involving cellular excitability or depolarization and damage resulting therefrom. Such neurodegenerative diseases include, for example, epilepsy, anoxia (which may be characterized by initial brief hyperpolarization followed by sustained depolarization of cells), hypoxia, convulsions, Parkinson's disease, Alzheimer's disease, and various forms of cerebral ischemia, including stroke and trauma. See, e.g., Gopalakrishnan et al., supra; Ben-Ari et al., *Neuroscience* 37: 55–60 (1990); Gandolfo et al., supra; Ashford et al., *Nature* 370: 456–59 (Aug. 11, 1994).

Additional diseases and disorders amenable to treatment with the peptides of the invention and methods of using these peptides are described below.

B. Representative Peptides of the Invention

Initially, certain peptides of the invention were isolated from a myocardial extract termed "Cardialin." Cardialin extract is described in USSR No. 1,417,242 (1988), incorporated herein by reference in its entirety for all purposes. This extract has been shown to prevent chemically induced cardiomyopathy (see USSR No. 2,007,157 (1992)), decrease tissue damage resulting from infarcts (Khavinson et al., Archive Pathology (USSR) 9: 27–31 (1989)), and depress lactic acid production in cardiac muscle slices by decreasing succinate dehydrogenase activity (Khavinson et al., USSR No. 1,807,399 (1993)). In addition, Cardialin (alternatively termed "Cordialin") has been shown to positively affect the energy metabolism of myocardial cells during hypoxia and ischemia. Pavlenko et al., Bull. Eksp. Biol. Med. (USSR) 112(7): 24–27 (1991); Pavlenko et al., Patol. Fiziol. Eksp. Ter. (Russia) 2: 20–24 (1992). Cardialin extract may also affect the ATP-sensitive potassium channels in cardiomyocytes. Babenko et al., Bull. Eksp. Biol. Med. (Russia) 114(7): 54–56 (1992). In prior studies, however, it has not been possible to determine whether these effects of cardialin were the result of a specific agent or a nonspecific insult.

In the present invention, cardialin extract was subjected the extract to high-pressure liquid chromatography (HPLC) fractionation using activation of cardiomyocyte adenylate cyclase activity as a screening assay to search for biologically active fractions (as described in Example 1 below). Isolated biologically active fractions were analyzed for peptide content using Edman degradation to determine the respective amino acid sequences of peptide fragments in the fractions. From the results obtained by these methods, candidate synthetic peptides were prepared and tested for their respective abilities to stimulate cardiomyocyte adenylate cyclase activity in isolated cardiomyocytes using radioimmunoassay. The synthetic peptides were then subjected to additional testing for pharmacological activity (as outlined in Examples 2 through 9 below).

Four peptides were identified by these methods. These peptides includes the dipeptides L-Gly-L-Glu and L-Val-L-Thr and the tetrapeptides L-Gly-L-Glu-L-Gly-L-Glu and L-Val-L-Thr-L-Val-L-Thr. These peptides are believed to activate and open potassium channels in cell membranes having potassium channels.

In one aspect of the invention, the peptides are characterized by their ability to activate or open potassium channels in cells having potassium channels in their cell membranes. Peptides of the invention are generally composed of a serial array of 16 or fewer naturally occurring (non-derivatized) L-amino acid residues peptide-bonded to one another. Preferably, a peptide of the invention is composed of fewer than about 9 to about 6 amino acid residues. More preferably, the peptide is composed of no more than 5 amino acid residues. The peptides typically have a molecular weight of less than about 4000 daltons. More preferably, these peptides have a molecular weight of less than about 2000 daltons and most preferably less than about 1000 daltons.

In another aspect, the peptides of the invention include L-Gly-L-Glu, L-Val-L-Thr, L-Gly-L-Glu-L-Gly-L-Glu, L-Val-L-Thr-L-Val-L-Thr, polymers of L-Gly-L-Glu comprising no more than 16 amino acid residues, polymers of L-Val-L-Thr comprising no more than 16 amino acid residues, and pharmaceutically acceptable salts thereof. The dipeptides L-Gly-L-Glu and L-Val-L-Thr are among the preferred dipeptides of the invention. L-Gly-L-Glu and L-Val-L-Thr are symbolized as GE and VT, respectively, according to IUPAC-IUB recommendations published in Arch. Biochem. Biophys. 115: 1–12 (1966). These dipeptides are available from Sigma Chemical Company (P.O. Box 14508, St. Louis, Mo. 63178–9916).

In another aspect, the invention provides peptide polymers comprising a serial array of 2, 3, 4, 5, 6, 7 or 8 dipeptides of L-Gly-L-Glu or L-Val-L-Thr, or any combination thereof, or pharmaceutically acceptable salts of such polymers, wherein the dipeptides are peptide-bonded to one another. The polymers may comprise at least two dipeptides, wherein each dipeptide of the polymer is L-Gly-L-Glu or L-Val-L-Thr. For example, polymers of the invention include the tetrapeptides L-Gly-L-Glu-L-Gly-L-Glu, L-Val-L-Thr-L-Val-L-Thr, L-Gly-L-Glu-L-Val-L-Thr, and L-Val-L-Thr-L-Gly-L-Glu.

Polymers of peptides of the invention, including polymers of L-Gly-L-Glu comprising no more than 16 amino acid residues, polymers of L-Val-L-Thr comprising no more than 16 amino acid residues, and polymers comprising L-Val-L-Thr and L-Gly-L-Glu and having more than 16 amino acid residues, and combinations thereof, are typically digested enzymatically in the blood or in living tissues or living organs into their respective dipeptides and tetrapeptides. The dipeptides and tetrapeptides that are released from such polymers by enzymatic digestion are expected to exert the same prophylactic and therapeutic effects as do the dipeptides and tetrapeptides of the invention, including the dipeptides L-Gly-L-Glu and L-Val-L-Thr and tetrapeptides formed from combinations of L-Gly-L-Glu and L-Val-L-Thr.

In another aspect, the peptides of the invention are characterized as being extractable from the myocardium at an acidic pH, including in a range of from about 2 to about 3.5, and isolatable therefrom in an included volume of a G-25 superfine chromatographic resin, having no effect on a tonic contraction of a smooth muscle specimen sample induced by a high potassium chloride concentration, and having a molecular size of less than about 15,000 daltons and most preferably less than about 5,000 daltons. Such a peptide may be termed a "myocardial peptide," since it is isolated from the myocardium. Alternatively, the subject peptides may be synthesized from naturally occurring amino acids and may comprise a serial array of no more than 16 L-amino acid residues.

Although the peptides of the invention are primarily described using the term of "peptide" or "peptides", one of skill in the art, upon reading the instant specification, will appreciate that these terms also include structural analogs and derivatives of the above-described peptides (e.g., peptides having conservative amino acid insertions, deletions or substitutions, peptidomimetics and the like). For example, in addition to the above-described peptides, which may comprise naturally-occurring amino acids, peptidomimetics of the peptides of the present invention are also provided. Peptide analogs are commonly used in the pharmaceutical industry as non-peptide drugs with properties analogous to those of the template peptide. These types of non-peptide compounds are termed "peptide milmetics" or "peptidomimetics" and are usually developed with the aid of computerized molecular modeling. Fauchere, J., Adv. Drug Res. 15: 29 (1986); Veber and Freidinger, TINS 392 (1985); and Evans et al., J. Med. Chem. 30: 1229 (1987). Peptide mimetics that are structurally similar to therapeutically or prophylactically useful peptides may be used to produce an equivalent therapeutic or prophylactic effect. Generally, peptidomimetics are structurally similar to a paradigm peptide (i.e., a peptide that has a biological or pharmacological activity), such as naturally-occurring peptide having potassium channel opener activity, but have one or more peptide linkages optionally replaced by a linkage selected from the group consisting of: —$CH_2NH$—, —$CH_2S$—, —$CH_2$—

CH$_2$—, —CH=CH— (cis and trans), —COCH$_2$—, —CH(OH)CH$_2$—, and —CH$_2$SO—. Such peptidomimetics may be generated by methods known in the art and further described in the following references: Spatola, A. F. in CHEMISTRY AND BIOCHEMISTRY OF AMINO ACIDS, PEPTIDES, AND PROTEINS 267 (B. Weinstein, eds. 1983); Spatola, A. F., *Vega Data* Vol. 1, Issue 3, "Peptide Backbone Modifications" (March 1983) (general review); Morley, J. S., *Trends Pharm Sci.*, pp. 463–468 (1980) (general review); Hudson, D. et al., *Int. J. Pept. Prot. Res.* 14: 177–185 (1979) (—CH$_2$NH—, CH$_2$CH$_2$—); Spatola, A. F. et al., Life Sci. 38: 1243–1249 (1986) (—CH$_2$—S); Hann, M., *J. Chem. Soc. Perkin Trans.* I 307–314 (1982) (—CH—CH—, cis and trans); Alnquist, R. G. et al., *J. Med. Chem.* (1980) 23: 1392–1398 (—COCH$_2$—); Jennings-White, C. et al., *Tetrahedron Lett.* 23: 2533 (1982) (—COCH$_2$—); Szelke, M. et al., European Appln. EP 45665 (1982) CA: 97: 39405 (1982) (—CH(OH) CH$_2$—); Holladay, M. W. et al., *Tetrahedron Lett.* 24: 4401–4404 (1983) (—C(OH)CH$_2$—); and Hruby, V. J., *Life Sci.* 31: 189–199 (1982) (—CH$_2$—S—).

Peptide mimetics may have significant advantages over peptide embodiments, including, for example: more economical production; greater chemical stability; enhanced pharmacological properties (half-life, absorption, potency, efficacy, etc.); altered specificity (e.g., a broad-spectrum of biological activities); reduced antigenicity; and others.

For some applications, it may also be desirable to provide the peptides of the invention as labeled entities, i.e., covalently attached or linked to a detectable group, to facilitate identification, detection and quantification of the peptide in a given circumstance. These detectable groups may comprise a detectable protein group, e.g., an assayable enzyme or antibody epitope as described above in the discussion of fusion proteins. Alternatively, the detectable group may be selected from a variety of other detectable groups or labels, such as radiolabels (e.g., $^{125}$I, $^{32}$P or $^{35}$S) or a chemiluminescent or fluorescent group. Similarly, the detectable group may be a substrate, cofactor, inhibitor or affinity ligand. Derivatization (e.g., labeling) of peptidomimetics should not substantially interfere with the desired biological or pharmacological activity of the peptidomimetic. Generally, peptidomimetics of peptides of the invention are believed to possess detectable biological activity (i.e., ability to activate and open potassium channels).

A pharmaceutically acceptable salt of a subject peptide may be readily prepared from a peptide (or its analog) by conventional methods. For example, such a salt may be prepared by treating the peptide with an aqueous solution of the desired pharmaceutically acceptable metallic hydroxide or other metallic base and then evaporating the resulting solution to dryness, preferably under reduced pressure in a nitrogen atmosphere. Alternatively, a solution of a peptide may be mixed with an alkoxide of the desired metal, and the solution subsequently evaporated to dryness. The pharmaceutically acceptable hydroxides, bases, and alkoxides encompass those with cations for this purpose, including, but not limited to, potassium, sodium, ammonium, calcium, and magnesium. Other representative pharmaceutically acceptable salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and the like.

It may be desirable to stabilize the peptides of the invention and their analogs or derivatives to increase their shelf life and pharmacokinetic half-life. Shelf-life stability is improved by adding excipients such as: a) hydrophobic agents (e.g., glycerol); b) sugars (e.g., sucrose, mannose, sorbitol, rhamnose, or xylose); c) complex carbohydrates (e.g., lactose); and/or d) bacteriostatic agents. The pharmacokinetic half-life of the subject peptides may be modified by coupling to carrier peptides, polypeptides, and carbohydrates using chemical derivatization (e.g., by coupling side chain or N- or C-terminal residues), or by chemically altering an amino acid of the subject peptide. The pharmacokinetic half-life and pharmacodynamics of these peptides may also be modified by: a) encapsulation (e.g., in liposomes); b) controlling the degree of hydration (e.g., by controlling the extent and type of glycosylation of the peptide); and c) controlling the electrostatic charge and hydrophobicity of the peptide.

Additional peptides of the invention may be identified by using conventional methods. These methods include screening for potassium channel opener activity by using standard assays, such as well-known patch-clamp assays and the assays described herein. Peptides of the invention may also be identified by screening combinatorial peptide libraries for peptides having potassium channel opener activities and/or one or more of the pharmacological activities typically exhibited by such peptides as described herein, including potassium channel activating activities. In addition, subject peptides may be identified by performing computer modeling of the three-dimensional space filled by a known peptide of the invention, such as L-Gly-L-Glu or L-Val-L-Thr, and constructing peptide mimetics. Furthermore, peptides of the invention may be identified by identifying or purifying a receptor of a known peptide of the invention and using the identified or purified receptor to isolate a peptide from a tissue, cell extract, or combinatorial peptide library. The assays disclosed herein may also be used to isolate and identify peptides of the invention.

Once a candidate peptide is isolated and its sequence is determined, a synthetic peptide having the same sequence may be prepared and tested for potassium channel opener activity and associated pharmacological activities. Candidate peptides may be synthesized by using any one of a number of different automated commercial techniques that are commonly available. These techniques typically involve stepwise synthesis of a peptide whereby amino acids are successively added to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. Blocking groups should be selected for easy removal without adversely affecting the peptides by racemization or by hydrolysis of the formed peptide bonds. Amino acids with carboxyl-groups (e.g., aspartic acid and glutamic acid) or hydroxyl-groups (e.g., serine, homoserine, and tyrosine) also require blocking prior to condensation.

A wide variety of procedures exist for synthesis of peptides, with solid-phase synthesis usually constituting the preferred method. With this method, an amino acid is bound to a resin particle, and the peptide generated in a stepwise manner by successive additions of protected amino acids to produce a chain of amino acids. Modifications of the technique described by Merrifield are commonly used. See, e.g., Merrifield, *J. Am. Chem. Soc.* 96: 2989–93 (1964), incorporated herein by reference in its entirety for all purposes. In an automated solid-phase method, peptides are synthesized by loading the carboxy-terminal amino acid onto an organic linker (e.g., PAM, 4-oxymethyl phenylacetamidomethyl), which is covalently attached to an insoluble polystyrene resin cross-linked with divinyl benzene. The terminal amine may be protected by blocking with t-butyloxycarbonyl. Hydroxyl- and carboxyl-groups are commonly protected by blocking with O-benzyl groups. Synthesis is accomplished in an automated peptide synthesizer, such as that available from Applied Biosystems. See, e.g., Model 430-A, Applied Biosystems, Foster City, Calif.

Following synthesis, the product may be removed from the resin. The blocking groups are removed by using hydrofluoric acid or trifluoromethyl sulfonic acid according to established methods. See, e.g., Bergot and McCurdy, *Applied Biosystems Bulletin* (1987). A routine synthesis may produce 0.5 mmole of peptide-resin. Following cleavage and purification, a yield of approximately 60 to 70% is typically produced. Purification of the product peptides is accomplished by, for example, crystallizing the peptide from an organic solvent such as methyl-butyl ether, then dissolving in distilled water, and using dialysis (if the molecular weight of the subject peptide is greater than about 500 daltons) or reverse high-pressure liquid chromatography (e.g., using a $C^{18}$ column with 0.1% trifluoroacetic acid and acetonitrile as solvents) if the molecular weight of the peptide is less than 500 daltons. Purified peptide may be lyophilized and stored in a dry state until use.

Once the amino acid sequence of a candidate peptide is known, the peptide may be prepared by using standard techniques of molecular biology, including expressing a portion of a nucleotide sequence of a genomic or cDNA clone that codes for the subject peptide. The nucleotide sequences may be incorporated into bacterial, yeast, or insect plasmid DNAs, as well as into mammalian cell viral vectors (e.g., retroviral vectors.) Expression systems that may be used to produce peptides include prokaryotic, eukaryotic, yeast, and insect cells. For example, repetitive G+E pairs of codons may be incorporated into linear nucleotide sequences, wherein each G+E pair of codons may optionally be separated from the next G+E pair of codons by a stop codons. The genetic code determines that the codons necessary for expression of the desired peptide.

The peptides of the invention are water-soluble at the low concentrations in which they are typically used. Such peptides are preferably used in the form of their acid or alkaline salts formed with pharmaceutically acceptable agents, such as acetic acid, citric acid, maleic acid, or succinic acid. Freely-soluble salts of the subject peptides may also be converted to salts of low solubility in body fluids by modification with a slightly water-soluble pharmaceutically acceptable salt (such as tannic acid or palmoic acid), by inclusion in a time-release peptide formulation (such as through covalent coupling to a larger carrier protein or peptide), or by inclusion in timed-release capsule and the like. In general, the acid salts of the peptides of the invention will be biologically and pharmacologically equivalent to the peptides themselves.

C. Pharmacological Activities of Peptides of the Invention

As noted above, the peptides of the invention exhibit a wide array of pharmacological and biological activities associated with the activation or opening of potassium channels. In one aspect, the peptides of the invention have the ability to regulate the functional activity of the smooth muscle of organs, as do known potassium channel openers. The potassium channel opener activities of these peptides may be measured by standard assays for measuring the increased outward flow of potassium ions from inside an electrically excitable test cell having a potassium channel in its cell membrane are well known to those skilled in the art. Such assays include standard patch-clamp assays, which are well known in the art.

Notably, the peptides of the invention are capable of inducing and producing relaxation of a variety of types of smooth muscle. As with standard potassium channel openers, the subject peptides inhibit spontaneous tension and contractile responses of smooth muscles and lower the spontaneous contractile activity of smooth muscle, while having no or minimal effects on potassium-induced tonic contraction of smooth muscles. The subject peptides also exhibit vasorelaxant effects, as evidenced by, for example, their ability to decrease the amplitude of spontaneous vascular smooth muscle contractions.

Peptides of the invention induce relaxation of smooth muscle by suppressing the amplitude of spontaneous contractions of smooth muscle in a manner similar to that of standard calcium channel blockers (such as Verapamil™). The suppression of spontaneous contraction of smooth muscle by these peptides is believed to be associated with one or more mechanisms of action. First, the administration of these peptides to a smooth muscle cell (or contact of these peptides with a smooth muscle cell) may produce a shift in the membrane resting potential of the smooth muscle cell toward a more negative value (i.e., hyperpolarization) by opening potassium channels in the cell membrane, thereby causing an increased outward flow of potassium ions from inside the cell to outside the cell via the channels during phases 3 and 4 of an action potential. Second, these peptides may accelerate a cell's repolarization, thereby vicariously influencing calcium ion influx via voltage-sensitive calcium channels and, ultimately, calcium ion release from sarcoplasmic reticulum essential for excitation-contraction coupling. Because smooth muscle cell excitability is dependent to a great extent on membrane resting potential, and smooth muscle cell contractile activity is dependent on intracellular calcium concentration, peptides acting through one or more of these two mechanisms may inhibit smooth muscle cell contractions in test assays.

Significantly, the peptides of the invention do not exert such suppressive effects in test assays in which the extracellular fluid has a high potassium ion concentration. This is generally considered to be an important feature of potassium channel openers. A high extracellular potassium ion concentration will typically shift the equilibrium membrane potential toward a more positive value, thereby inducing contraction. Under such conditions, a peptide having potassium channel opener activity may fail to inhibit a cell's contractile activity. Under such circumstances, although the potassium channels of a cell membrane are activated, potassium ions in the cell cannot flow outward against the concentration gradient.

The relaxation and contraction of smooth muscle may be observed by a variety of well known methods. For example, the relaxation of gastrointestinal smooth muscle may be clinically observed by examination of the abdomen or by various radiographic methods, such as contrast dye studies, barium enemas, and the like, or by measuring a reduction in peristaltic activity (for example, by using a stethoscope to monitor peristaltic activity).

In another aspect, the peptides of the invention exhibit pharmacological activities of anti-ischemic agents, as is observed with certain known potassium channels openers. Importantly, the subject peptides restore the inotropic function of ischemic myocardium, without inducing arrhythmia. The subject peptides optimize contractile work of the ischemic muscle and restore contractile function to pre-ischemic levels as evidenced by their ability to: (i) restore cardiac differential pressures; (ii) inhibit premature ventricular contractions (PVCs); (iii) restore diastolic pressures to normal values; and (iv) restore the developmental pressure and contractile force of the left ventricle. The subject peptides display positive inotropic activity in ischemic myocardium (i.e., they increase cardiac work efficiency as measured by increased cardiac output without increased oxygen consumption, increased metabolic rate, or induction of arrhythmia), and weak negative chronotropic activity when injected intraperitoneally or intravenously, or when introduced into the cardiac circulation (i.e., through the aorta) at certain concentrations (e.g., about $10^{-5}$ to $10^{-7}$M). As used herein, an increase in cardiac work efficiency refers to an ability to perform more cardiac work with less energy expenditure, as may be measured by, for example, determining the volume of blood output from a heart beating at a particular rate over a lefmed period of time. In addition, the peptides of the invention exhibit a weak negative or null chronotropic activity (i.e., the subject peptides do not increase heart rate, but instead decrease heart rate or have no effect on heart rate). As used herein, the term "chronotropic" means affecting the rate of rhythmic movements, such as the rate of the heart beat or cardiac contractions. The term "positive chronotropic" means increasing the rate of rhythmic movements (e.g., increasing the rate of the heart beat or cardiac contractions). The term "negative chronotropic" means decreasing the rate of rhythmic movement (e.g., decreasing the rate of cardiac contractions or heart beat).

Peptides of the invention lessen the extent of ischemic myocardial lesions without adversely affecting inotropic functions of the heart, as is evidenced by low levels of enzymatic activities of certain intracellular myocardial enzymes in blood following the onset of ischemia, as is discussed in more detail below.

The subject peptides act as antiarrhythmic agents, reducing the incidence of premature ventricular contractions or episodes of ventricular tachycardia or ventricular fibrillation. Significantly, the subject peptides have no affect on normal cardiac functioning.

Peptides of the invention also exert cardioprotective effects that are similar to those generally observed with known potassium channel openers. Such cardioprotective effects include: (1) restoring the inotropic function of ischemic myocardium (which may be evaluated by measuring ventricular systolic and diastolic pressures, ventricular evolving pressure, and maximum ventricular pressure elevation and reduction rates), but not inducing arrhythmia; (2) promoting anti-ischemic effects by decreasing the extent of ischemia in a tissue or organ or decreasing the extent of myocardial lesions in the heart following an interruption of blood flow to the heart muscle (such as following coronary occlusion) without adversely effecting the inotropic functions of the heart; (3) preventing the development of arrhythmias (or dysrhythmias), where chloroform or coronary occlusion was used to induce arrhythmia (or dysrhythmia), as reflected in a reduction of the number of premature ventricular contractions or decreasing the total duration of episodes of ventricular tachycardia or ventricular fibrillation; (4) producing vasodilating effects, including coronarodilatory activity and hypotensive effects; (5) having minimal or no effect on the inotropic function of the myocardium or on the heart rate of a normal heart; and (6) having minimal or no influence on electrophysiological parameters of the normal heart, as reflected by normal myocardial electrocardiogram measurements.

Test assays for evaluating heart functions are also well known to those skilled in the art. For instance, electrocardiogram (ECG) monitoring is routinely used to identify and measure premature ventricular contractions, ventricular tachycardia, and ventricular fibrillations. The extent of ischemia in a tissue or organ of a subject may be determined by gross pathologic examination, histologic examination, or measurement of an organ activity in vivo or in vitro. Cardiac organ activity may be determined by various commonly known methods (such as by measuring the heart rate, or the diastolic, systolic, differential or developmental pressure in the heart chambers, or by measuring the level of cardiac muscle enzymes, such as creatinine phosphokinase, in the blood).

As noted above, the peptides of the invention reduce the spontaneous contractile activity of vascular smooth muscle. However, in noteworthy contrast to calcium blockers, the subject peptides exert no effect on tonic contraction induced by high potassium chloride concentrations. The subject peptides exhibit vasodilating activities and are capable of decreasing the mean arterial blood pressure in subjects in need of such treatment. These vasodilating activities include coronarodilating activities (i.e., increasing the cross-sectional area of a coronary blood vessel, as in, for example, a coronary artery) and hypotensive activities (i.e., causing reduction in blood pressure).

Assays for measuring the vasodilating and anti-arrhythmic effects of substances are well known in the art and include those assays illustrated below. As noted above, vasodilation may increase the volume of blood flowing through a vessel and/or decrease blood pressure in the vessel. Vasodilation may be detected and measured by a variety of standard clinical techniques and measurements. For example, vasodilation is indicated where a subject shows an increase in erythema (e.g., a redness of the skin due to an increase in blood flow to the skin or "blushing"), a decrease in blood pressure, an increase in warmth of the target skin, or vascular engorgement. Vascular engorgement, which serves as an indication of vasodilation, can be readily observed in superficial veins. Blood flow may be measured by standard methods, including conventional pressure-cuff blood pressure measurements and pressure transducer measurements. Illustrative assays for detecting and measuring vasodilation are also presented in the examples below.

Additionally, the subject peptides induce and produce relaxation of skeletal muscle, as evidence by their ability to decrease the amplitude of calcium-induced intestinal smooth muscle contractions. As with smooth muscle tissue, these peptides are believed to induce relaxation of skeletal muscle by activating or opening potassium channels of skeletal muscle. Assays for measuring contraction and relaxation of skeletal muscle are well known to those of skill in the art and include those described above.

Given their smooth-muscle relaxant activities, the peptides of the invention are also expected to relax airway smooth muscle (such as tracheal smooth muscle) and to exhibit bronchodilating effects on bronchial smooth muscle. These bronchodilatory effects are believed to be mediated through a common mechanism involving restoration of the normal pattern of electrophysiological functioning in the electrically excitable cells of a pathologically-altered tissue (e.g., pathologically changed bronchial smooth muscle). Test assays for measuring relaxation of airway smooth muscle and bronchodilating effect, as in ex vivo or in vivo lung function assays, are well known in the art.

In addition, due to their smooth-muscle relaxant effects, the peptides of the invention are anticipated to exert relaxant effects on the myometrium during pregnancy and to alleviate premenstrual cramps and premature uterine contractions. Such effects may be readily measured by procedures well known to one of skill in the art.

Due to their potassium channel activating activities, the peptides of the invention are believed to reduce neuronal excitability and to exhibit anticonvulsant effects on brain cells. Electrical activity of the brain may be measured by using electroencephalographic techniques, PET-scan, and the like.

As anti-ischemic agents, the peptides of the invention act to preserve tissues and organs. The preservation effects of these peptides are believed to be associated with their potassium channel opener properties and their ability to regulation potassium channels. Test assays for evaluating such preservation effects are generally known in the art and include those described above.

Illustrative assays for detecting and measuring the pharmacological and biological activities of the peptides of the invention are provided in the examples below.

III. PHARMACEUTICAL COMPOSITIONS

The invention provides pharmaceutical compositions in unit dosage form comprising the peptides of this invention. These peptides are useful for treating or preventing diseases responsive to the opening of potassium channels in a subject in need thereof, as described above. In particular, pharmaceutical compositions comprising the peptides of the invention are useful for treating or preventing cardiovascular diseases, inducing and producing relaxation of smooth muscle, and inducing and producing relaxation of skeletal muscle. Pharmaceutical compositions of the invention in unit dosage form generally comprise per unit dosage a range of from about 0.01 mg to about 1000 mg of L-Gly-L-Glu or L-Val-L-Thr or a pharmaceutically acceptable salt thereof and a pharmaceutically acceptable carrier. In a preferred aspect of the invention, the composition comprises per unit dosage a range of from about 1 mg to about 100 mg of L-Gly-L-Glu, L-Val-L-Thr, or a pharmaceutically acceptable salt thereof, and a pharmaceutically acceptable carrier.

The preferred form of these pharmaceutical compositions depends on the intended mode of administration and therapeutic application. The compositions may include (depending on the formulation desired) pharmaceutically acceptable, non-toxic carriers or diluents, which are defined as vehicles commonly used to formulate pharmaceutical compositions for animal or human administration.

IV. APPLICATIONS

A. Therapeutic and Prophylactic Methods

This invention provides methods for therapeutically or prophylactically treating diseases and disorders responsive to, sensitive to, or associated with the opening of potassium channel in subjects in need of such treatment. These subjects may include humans and animals, particularly vertebrate mammals. The principal therapeutic and prophylactic areas of use for these peptides include treatments designed to accomplish the following effects: (1) vasodilatory effects, including coronarodilation and hypotensive effects (e.g., using the subject peptides to treating subjects suffering from cardiac insufficiency or to preventing cardiac insufficiency in subjects in need thereof); (2) anti-ischemic cardioprotective effects, which include lessening the extent of ischemic myocardial lesions without adversely effecting inotropic functions of the heart (e.g., using the subject peptides to treat subjects following stroke and heart attack); (3) bronchodilatory effects (e.g., using the peptides to treat or prevent asthma, bronchospastic disorders, or bronchospastic syndrome and/or to induce relaxation of bronchial smooth muscle); (4) smooth muscle relaxatory effects (e.g., using the peptides to treat abnormal pregnancies, including conditions involving premature uterine contractions and premenstrual cramps, and to relax the myometrium of subjects during pregnancy); (5) skeletal muscle relaxatory effects; (6) anti-epileptic and anticonvulsant effects; (7) reduction of neuronal excitability; and (8) regulating insulin secretion. Importantly, peptides of the invention are able to produce these effects at low dosage levels and without toxic side effects.

In one aspect, this invention provides methods for the prophylactic or therapeutic treatment of diseases and disorders that are treatable by, responsive to, or sensitive to the opening of potassium channels in cell membranes of subjects in need of such treatment. Representative diseases and disorders are discussed below. These methods comprise administering to a subject in need thereof, including a human, an effective amount of a peptide of the invention as described above. Generally, the peptide may comprise L-Gly-L-Glu, L-Val-L-Thr, a polymer of L-Gly-L-Glu comprising no more than 16 amino acid residues, a polymer of L-Val-L-Thr comprising no more than 16 amino acid residues, a polymer of L-Val-L-Thr and L-Gly-L-Glu comprising no more than 16 amino acid residues, or a pharmaceutically acceptable salt thereof. In addition, the peptide may comprise a polymer of L-Val-L-Thr and L-Gly-L-Glu that comprises no more than 16 amino acid residues.

In another aspect, the invention provides methods specifically directed to treating and preventing cardiovascular diseases associated with potassium channels or responsive to the opening or activation of potassium channels. Such cardiovascular diseases are discussed in detail below. These methods comprise administering to a subject in need thereof, including a human, an effective amount of a peptide of the invention as described above. The peptide typically comprises L-Gly-L-Glu, L-Val-L-Thr, a polymer of L-Gly-L-Glu comprising no more than 16 amino acid residues, a polymer of L-Val-L-Thr comprising no more than 16 amino acid residues, or a pharmaceutically acceptable salt thereof. The peptide may comprise a polymer of L-Val-L-Thr and L-Gly-L-Glu having no more than 16 amino acid residues.

The present invention also includes methods for inducing and producing relaxation of smooth muscle in subjects in need of such treatment. In yet another embodiment, the invention provides methods for inducing and producing relaxation of skeletal muscle in subjects in need thereof. Both of these methods comprise administering to the subject, which may be a human, an effective amount of a peptide of the invention, as described above. Usually, the peptide comprises L-Gly-L-Glu, L-Val-L-Thr, a polymer of L-Gly-L-Glu comprising no more than 16 amino acid residues, a polymer of L-Val-L-Thr comprising no more than 16 amino acid residues, or a pharmaceutically acceptable salt thereof. The peptide may comprise a polymer of L-Val-L-Thr and L-Gly-L-Glu having no more than 16 amino acid residues. Such methods may be employed to relax various types of smooth muscle, including intestinal, bronchial, tracheal, uterine, bladder, bowel, vas deferens, and vascular smooth muscle.

Also provided are methods for the prophylactic or therapeutic treatment of diseases responsive to opening of potassium channels which comprise administering to subjects in need thereof an effective amount of a peptide having a potassium channel opener activity, wherein the peptide comprises a serial array of no more than about 16 L-amino acid residues, is extractable from myocardium in an acidic extract and isolatable therefrom in an included-volume of a G-25 superfine chromatographic resin, and has no effect on a tonic contraction of a smooth muscle specimen induced by a high potassium concentration. In such methods, the potassium channel opener activity comprises an increased flow of potassium ions from inside an electrically excitable cell to outside the cell via a membrane of the cell that has at least one potassium channel.

B. Diseases and Disorders Amenable to Treatment

Due to their ability to activate and open potassium channels, the peptides of this invention are useful for treating or preventing a wide array of diseases and disorders responsive or sensitive to the opening of potassium channels or associated with potassium channel opener activities (including those diseases or disorders in which the cell membrane of tissue or organ of the subject is partly depolarized, e.g., as in ischemic tissues or organs).

Peptides of the invention are effective in treating and alleviating cardiovascular diseases that are associated with potassium channels or are responsive to potassium channel activation. The subject peptides are especially useful in treating and preventing all forms of ischemic heart disease described herein (including myocardial infarction, angina pectoris, acute and chronic coronary insufficiency, and post-myocardial infarction cardiosclerosis). The subject peptides also function successfully as anti-ischemic and cardioprotective agents to lessen the extent of ischemic lesions in the heart, without adversely effecting the respective inotropic functions of the heart, as discussed above. Notably, the peptides of the invention restore and improve mechanical cardiac function following the onset of ischemia and inhibit cardiac contracture formation. The cardioprotective effects of these peptides are associated with, in part, their ability to regulate and activate potassium channels in ischemic myocardial tissue (i.e., to hyperpolarize or inhibit further depolarization of potassium-channel bearing cells in ischemic tissue). These peptides aid in preventing damage to the heart which typically occurs during various cardiac malfunctioning (e.g., acute myocardial infarction).

The subject peptides also protect the heart by providing it with an ability to better withstand transient oxygen deprivation. A characteristic of myocardial cell damage in ischemia and hypoxia is the disturbance of the respiratory function of the mitochondria or an interruption in or blockage of the oxygen supply to myocardial cells. The vasodilating effects of these peptides may result in an increased flow of blood and oxygen to the heart.

The peptides of the invention are also useful in treating and preventing other cardiovascular diseases associated with potassium channels or responsive to potassium channel activation. Such diseases include, but not limited to, cardiac dysrhythmias (including rhythm paroxysmal tachycardia and other forms of tachycardia, such as ventricular tachycardia, ventricular fibrillation, supraventricular and ventricular ectopy, and unspecified premature beats); cardiac arrhythmias, cardiomyopathy and myocardial dystrophy; all types of hypertensive disease; congestive heart failure; hypoxia; cardiovascular diseases resulting from exposure to chemical toxins; cardiac insufficiency; and cardiovascular diseases associated with conduction disorders (i.e., AV-blocks of different grades of severity). See, e.g., Guermonprez et al., supra. Additionally, because the peptides of the invention are effective antiarrhythmic, vasodilating, coronarodilatory, or hypotensive agents, they may be useful in treating and preventing cardiovascular diseases (and related disorders) that may benefit from such effects.

Additionally, peptides of the invention are useful for inducing and causing relaxation of smooth muscle and for treating and preventing diseases, disorders, and disorders associated with smooth muscle contractions and diseases responsive to moderation of the smooth-muscle contractile response. The subject peptides are helpful for relaxing vascular smooth muscle and blood vessel walls and for treating and preventing diseases, disorders, and disorders associated with vascular smooth muscle pathology.

Peptides of the invention are also useful for relaxing nonvascular smooth muscle (such as the trachea, bronchi, urinary bladder, intestine, uterus, vas deferens) and for treating and preventing disorders, conditions, and diseases of nonvascular smooth muscle, including hyper-reactive disorders of nonvascular smooth muscle (such as asthma, irritable bowel, irritable bladder), hyper-reactive conditions in the lung and gastrointestinal tract, and various allergic conditions associated with abnormally increased smooth muscle reactivity (e.g., asthma and bronchospastic disorders). With their smooth muscle relaxant properties, the subject peptides are useful in treating, preventing, and alleviating premenstrual cramps, premature uterine contractions, and/or complications resulting from an increased tone of the myometrium.

As noted above, the peptides of the invention are anticipated to relax airway smooth muscle (e.g., bronchial smooth muscle tissue) and exhibit bronchodilatory effects, as do known potassium channel openers. The subject peptides are anticipated to be of benefit in treating, managing, and preventing disorders associated with bronchial asthma, including bronchoconstriction, bronchospastic conditions, and bronchospastic syndrome and the like. Bronchodilation is indicated by improved respiration in an asthmatic patient and can be measured by a variety of standard pulmonary function tests, such as forced expiratory volume ($FEV_1$).

Since these peptides relax smooth muscle and inhibit the contraction of smooth muscle, they are useful in treating and preventing pathological conditions, states, or diseases that generally result from or involve pathological vascular smooth muscle contraction or smooth muscle over-reactivity (e.g., hypertension). Similarly, the subject peptides are useful in treating and preventing peripheral vascular disease and conditions in which a reduction in a reduction peristaltic activity is desired.

Additionally, because the peptides of the invention relax vascular smooth muscle and induce vasodilation, they are useful in the prophylactic and therapeutic treatment of diseases or disorders that are treatable by, responsive to, or sensitive to vasodilation. For example, they are of benefit in treating and preventing hypertension, high blood pressure, peripheral vascular disease, and the like. Importantly, vasodilation increases and restores the flow of blood, oxygen, and nutrients to damaged tissues (such as ischemic tissues) and tissues that have been deprived of blood, oxygen, and nutrients (such as tissues having zones of hypoxia), and cell death can be prevented, slowed, or delayed. As a result, the subject peptides, with their vasodilating properties, are effective in preventing and slowing cell death in tissues that have been deprived of blood, oxygen, and nutrients, and in treating and preventing disorders resulting from such circumstances (e.g., hypoxia, anoxia, ischemia).

Furthermore, peptides of the invention are useful for inducing relaxation of skeletal muscle and for treating and preventing diseases and disorders associated with skeletal muscle contraction and diseases responsive to moderation of the skeletal-muscle contractile response, including certain skeletal muscle myopathies and ischemic skeletal muscle conditions. Carmeliet, *Eur. Heart J.* 12 (Suppl. F): 30–37 (1991); McPherson, *Gen. Pharnac.* 24(2): 275–81 (1993).

Given their smooth muscle relaxant properties and vasodilating effects, the subject peptides are expected to be useful in treating and preventing cirrhosis of the liver.

Cirrhosis of the liver is a chronic disease of the liver marked by progressive destruction and regeneration of liver cells and increased connective tissue formation that ultimately results in blockage of portal circulation, portal hypertension, liver failure, and death. By inducing smooth muscle relaxation and vasodilation, the subject peptides act to divert blood supply away from the portal vein and thus inhibit or slow the progress of cirrhosis. Liver activity may generally be determined by measuring the levels of enzymes (such as alkaline phosphatase) in peripheral blood.

Potassium channels are widely distributed in brain cells and have been implicated in various brain disorders, including epilepsy, anoxia, various neurodegenerative diseases, Parkinson's disease, Alzheimer's disease, and various forms of cerebral ischemia, including stroke and trauma. See, e.g., Gopalakrishnan et al., supra; Ben-Ari et al., *Neuroscience* 37: 55–60 (1990); Gandolfo et al., supra; Ashford et al., *Nature* 370: 456–59 (Aug. 11, 1994). Known potassium channel openers have been found to reduce neuronal excitability and to have anticonvulsant effects on brain cells. The effects of known potassium channels on brain cells may be due to several mechanisms of action. As in other tissues having cells with potassium channels, the direct activation of potassium channels in brain cells appears to reduce such cells' excitability and protect such cells.

Potassium channel openers may also benefit brain tissues through their vasodilating properties. Some neurodegenerative diseases are characterized, at least in part, by a lack of oxygen and nutrients in neuronal tissue. It is known that a progressive lack of oxygen and nutrients in brain and neuronal tissues promotes the progression of neurodegenerative disease. By improving the delivery of oxygen and nutrients to neuronal tissue, neurodegenerative diseases may be slowed and stabilized. Vasodilation generally increases circulation and blood flow and improves produces oxygen and nutrient delivery to body tissues. With their vasodilating effects, potassium channel openers may assist in retarding and stabilizing neurodegenerative diseases, by increasing the flow of oxygen and nutrients to brain tissues in need thereof.

Given their vasodilating properties, peptides of the invention are expected to be useful in treating and preventing variety of brain disorders resulting from, for example, excessive or improper neuronal excitability. The subject peptides are anticipated to reduce neuronal excitability and to have anti-ischemic and anticonvulsant effects on brain cells having potassium channels. Thus, the subject peptides should be useful in treating and preventing disorders associated with neuronal damage and excessive or improper excitability, including epilepsy, anoxia, hypoxia, stroke, trauma, cerebral ischemia, convulsions, and Alzheimer's disease.

Further, as vasodilators, the peptides of the invention increase the flow of blood and the delivery of oxygen and nutrients to neuronal tissues, and thus improve the quality and stability of neuronal tissues and are expected to slow the progression of neurodegenerative diseases. Thus, the subject peptides are of benefit in treating and preventing disorders that result from a lack of or deprivation of oxygen and nutrients in tissues. For these reasons, the subject peptides are useful in treating and preventing anoxia (e.g., cardiac hypoxia and neuronal hypoxia), hypoxia (e.g., cardiac hypoxia and neuronal hypoxia), Parkinson's disease, and Alzheimer's disease. In addition, because epilepsy may be triggered by a lack of oxygen and/or may result from hypoxic conditions, the subject peptides are expected to be useful in treating and preventing epilepsy and related disorders. Likewise, the subject peptides are also useful in treating and preventing cardiac ischemia, since during cardiac ischemia myocytes undergo oxygen deprivation and suffer from the interruption of perfusion.

Moreover, because potassium channels may form a feedback loop with pancreatic beta cells to regulate appetite, the subject peptides are expected to be helpful in treating and preventing appetite and feeding disorders and diseases. Gopalakrishnan et al., supra. Furthermore, because potassium channels may be associated with diabetes and related disorders, the peptides of the invention are believed to be useful in treating and preventing diabetes. See, e.g., Ashford et al., supra.

The peptides are also anticipated to be helpful in treating and preventing kidney diseases. Kidney activity may be measured by monitoring the level of urea nitrogen in blood. Peptides of the invention are also of benefit for preserving and maintaining living tissues and organs ex vivo. For example, such peptides may be used for preserving a living tissue and organ, such as a heart or blood vessel, ex vivo prior to transplantation (or re-implantation) into a subject.

C. Dosages and Methods of Administration

In therapeutic applications, a peptide of the invention may be administered to a subject already suffering from an undesirable disease or condition (e.g., ischemic heart disease), in an amount sufficient to treat, cure, partially arrest, or detectably slow the progression of the disease and its complications. An amount of a peptide of the invention effective for use in therapeutic applications will depend upon the severity of the condition, the general state of the subject, and the route of administration. The effective amount of the peptide in therapeutic applications will generally be within a range from about 0.15 microgram per kilogram (mg/kg) to about 10 mg/kg of the peptide (or a pharmaceutically acceptable salt thereof) per dose. The effective amount of the subject peptide may range from about 0.01 mg/kg to about 10 mg/kg per dose. An effective amount of L-Gly-L-Glu or L-Val-L-Thr, or a pharmaceutically acceptable salt thereof, for use in therapeutic applications may range from about 0.15 mg/kg to about 10 mg/kg of the respective peptide (or a pharmaceutically acceptable salt thereof) per dose.

In prophylactic applications, the subject peptides or pharmaceutical compositions thereof are administered to subjects at risk of, but not already suffering an undesired disease or condition. The effective amount of peptide to be administered will depend upon the subject's state of health and general level of immunity. The effective amount of the peptide in prophylactic applications will generally be within a range from about 0.15 microgram per kilogram (mcg/kg) to about 10 mg/kg of the peptide per dose. The effective amount may range from about 0.01 mg/kg to about 10 mg/kg of active agent per dose. In prophylactic applications, an effective amount of L-Gly-L-Glu or L-Val-L-Thr, or a pharmaceutically acceptable salt thereof, may range from about 0.15 mg/kg to about 10 mg/kg of the respective peptide (or a pharmaceutically acceptable salt thereof) per dose.

In methods of inducing relaxation of smooth muscle in subjects in need thereof and methods of inducing relaxation of skeletal muscle in subjects in need thereof. For each of these methods, an effective amount of the peptide will generally be within a range from about 0.15 microgram per kilogram (mcg/kg) to about 10 mg/kg of the peptide per dose. The effective amount of the subject peptide may range from about 0.01 mg/kg to about 10 mg/kg per dose. In methods of inducing relaxation of smooth muscle or skeletal muscle, an effective amount of L-Gly-L-Glu or L-Val-L-Thr, or a pharmaceutically acceptable salt thereof, may range from about 0.15 mg/kg to about 10 mg/kg of the respective peptide per dose.

Alternatively, pharmaceutical compositions in unit dosage form may be administered in the above applications, including in prophylactic treatment regimens. In one embodiment, these pharmaceutical compositions may comprise per unit dosage an effective amount of from about 0.01 mg to about 1000 mg of L-Gly-L-Glu or L-Val-L-Thr (or a pharmaceutically acceptable salt thereof) and a pharmaceutically acceptable carrier. In another embodiment, such compositions may comprise per unit dosage an effective amount of from about 1 mg to about 100 mg of L-Gly-L-Glu or L-Val-L-Thr (or a pharmaceutically acceptable salt thereof), respectively, and a pharmaceutically acceptable carrier.

The preferred form of the subject peptides for inocula and dosage will vary with the clinical indication. The inocula is typically prepared from a dried peptide (or its conjugate) by suspending the peptide in a physiologically acceptable diluent such as water, saline, or phosphate-buffered saline. Some variation in dosage will necessarily occur depending upon the condition of the subject being treated, and the physician will determine the appropriate dose for the individual subject. The effective amount of peptide per unit dose will depend, among other things, on the body weight and physiology of the subject and the chosen inoculation regimen. A unit dose of the peptide refers to the weight of peptide without the weight of a carrier (when a carrier is used). For a pharmaceutical composition in unit dosage form, an effective therapeutic or prophylactic treatment will typically be achieved by administering within a range of from about 0.01 mg to about 1000 mg of the peptide (or a pharmaceutically acceptable salt thereof) per dose, with single dosage units of the peptide of from about 1 mg to about 100 mg. The pharmacologically effective amount of L-Gly-L-Glu or L-Val-L-Thr (or a pharmaceutically acceptable salt thereof) is generally within a range of from about 0.01 mg to about 1000 mg of the subject peptide per unit dose. Usually, the pharmacologically effective amount of L-Gly-L-Glu or L-Val-L-Thr (or a pharmaceutically acceptable salt thereof) is within a range of from about 1 mg to about 100 mg per unit dose.

The route of delivery of the peptides and pharmaceutical compositions of the invention is determined by the disease or clinical indication and the site where treatment is required. For topical application, it may be desirable to apply the peptide or composition thereof at the local site (for example, by using a catheter placed in the coronary artery during surgery, or by applying a surgical bandage impregnated with the peptide on the myocardial tissue to be treated during cardiac surgery). Alternatively, with advanced diseases, it may be desirable to administer the peptide or composition systemically.

For other indications, peptides and pharmaceutical compositions of the invention may be delivered by intravenous, intraperitoneal, intramuscular, subcutaneous, intranasal, and intradermal injection, as well as by intrabronchial instillation (e.g., by using a nebulizer), and transmucosal, systemic, transdermal (e.g., with a lipid-soluble carrier in a skin patch), oral, and gastrointestinal delivery (e.g., with a capsule or tablet). During or after cardiovascular surgery (e.g., cardiac bypass surgery, angioplasty, and the like), peptides and pharmaceutical compositions may be administered in an intravenous bolus injection (or by perfusion).

One or more peptides of the invention may be administered in combination therapy. For example, one or more subject peptides may be administered in combination with an anti-coagulant (such as streptokinase/streptodornase, tissue plasminogen activator, or urokinase) to a subject in need of such treatment, such as a subject who has previously experienced an episode of coronary thrombosis.

The pharmacokinetics and pharmacodynamics of peptides of the pharmaceutical compositions will vary in different subjects. In an acute setting, it may be desirable to achieve a therapeutic or prophylactic concentration of the peptide in an organ, at a tissue site to be treated, or in the blood of the subject being treated by administering the peptide or composition thereof to the subject in a manner that the concentration of the peptide to increase rapidly in the tissue, organ, or blood. For example, the concentration of a peptide at a particular site may be increased rapidly by bolus intravenous injection or infusion of the peptide or a pharmaceutical composition thereof. Alternatively, a therapeutic or prophylactic concentration of the peptide may be achieved in an organ, at a tissue site to be treated, or in the blood of the subject by administering an increasing amount or dosage of the peptide (or pharmaceutical composition thereof) over a period of time until an effective amount of the peptide is achieved in the organ, tissue site, or blood. The initial dose for this type of regimen will depend upon the route of administration. By way of example, for intravenous administration of a pharmaceutical composition comprising a peptide having a molecular weight of from about 200 to about 400 daltons, an initial dosage of from about 0.001 mg/kg to about 10 mg/kg may be initially administered. With each subsequent administration, the dosage may be increased by increasing the peptide concentration by a factor or 10.

The peptides of the invention may be administered alone or in combination with a pharmaceutically acceptable carrier as in the pharmaceutical compositions described above. The peptides may be administered single or multiple doses. Suitable pharmaceutical carriers include inert solid diluents or fillers, sterile aqueous solutions, and various nontoxic organic solvents. The pharmaceutical compositions formed by combining a subject peptide with a pharmaceutically acceptable carrier may be readily administered in a variety of dosage forms such as tablets, lozenges, syrups, injectable solutions, and the like. If desired, the pharmaceutical carriers may contain additional ingredients, such as flavorings, binders, excipients, and the like.

For oral administration, tablets containing various excipients, such as sodium citrate, calcium carbonate, and calcium phosphate, may be employed along with various disintegrants, such as starch, and preferably potato or tapioca starch, alginic acid, and certain complex silicates, together with binding agents, such as polyvinylpyrrolidone, sucrose, gelatin, and acacia. Lubricating agents, such as magnesium stearate, sodium lauryl sulfate, and talc, are also added for tableting purposes. Solid compositions of a similar type may also be employed as fillers in salt and hard-filled gelatin capsules. Preferred materials for this purpose include lactose or milk sugar and high molecular weight polyethylene glycols. When aqueous suspensions of elixirs are desired for oral administration, the essential active peptide ingredient therein may be combined with various sweetening or flavoring agents, colored matter or dyes, and, if desired, emulsifying or suspending agents, together with diluents such as water, ethanol, propylene glycol, glycerin, and combinations thereof.

For parenteral administration, solutions of the peptide (or its analog) in sesame or peanut oil or in aqueous polypropylene glycol may be employed, as well as sterile aqueous saline solutions of the corresponding water soluble pharmaceutically acceptable metal salts previously described. Such an aqueous solution should be suitably buffered if necessary, and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art. Additionally, the aforesaid compounds may be administered topically (for example, through a placed catheter) by using an appropriate solution suitable for the particular purpose. Parenteral solutions can be formulated with about 0.001–10 mg/ml of the peptide in combination with a pharmaceutically acceptable carrier in a solution of sterile physiological saline and administered to a subject in need thereof to achieve a dosage of about 0. 1–10 mg/kg.

V. METHODS OR PRESERVING LIVING TISSUES AND ORGANS

Peptides of the invention provides are useful for preserving and storing living tissues or organs ex vivo in various applications. For example, these peptides are useful for preserving and maintaining a living tissue and organ, such as a heart or blood vessel, ex vivo prior to transplantation (or re-implantation) into a subject. These peptides are also useful for preserving and maintaining living tissues and organs under ischemic conditions. Methods of preserving living tissues and organs typically comprise contacting the tissue or organ with a composition comprising a pharmaceutically acceptable carrier and an effective amount of a peptide of the invention. Such peptides generally comprise L-Gly-L-Glu, L-Val-L-Thr, a polymer of L-Gly-L-Glu comprising no more than 16 amino acid residues, a polymer of L-Val-L-Thr comprising no more than 16 amino acid residues, or a combination thereof, or a pharmaceutically acceptable salt thereof. L-Gly-L-Glu and L-Val-L-Thr and polymers thereof are among the preferred peptides for use in such methods. For these methods, the effective amount of L-Gly-L-Glu or L-Val-L-Thr is the amount that is sufficient to produce a concentration of the peptide of from about $10^{-9}$M to about $10^{-5}$M at the tissue or organ site to be treated. Additional peptides for use in methods of preserving and storing living tissues and organs may be identified and synthesized as described above.

VI. KITS FOR PRESERVING LIVING TISSUES AND ORGANS

The invention also provides kits useful for preserving living tissues or organs. These kits include an effective amount of L-Gly-L-Glu, L-Val-L-Thr, or a pharmaceutically acceptable salt thereof. The effective amount of L-Gly-L-Glu or L-Val-L-Thr is generally within a range of from about $10^{-9}$M to about $10^{-5}$M. Alternatively, such kits may include a polymer of L-Gly-L-Glucor L-Val-L-Thr, or a combination thereof, wherein the polymer comprises no more than 16 amino acid residues. Such kits may also include a container for holding the peptide and the tissue or organ.

The present invention is further illustrated by the following examples. These examples are merely to illustrate aspects of the present invention and are not intended as limitations of this invention.

EXAMPLES

Example 1

Isolation, Purification, and Characterization of Peptides of the Myocardium Having Potassium Channel Opener Activity The dipeptides of the invention, GE and VT, and two tetrapeptide polymers of these dipeptides were identified, isolated, and purified as follows.

Approximately 0.5 gram (g) of a bovine heart tissue extract of low molecular weight was prepared in zinc chloride (ZnCl) at a pH of 2 to 3 by following a procedure similar to that disclosed in USSR Patent No. 1,417,242 (1988), which is incorporated herein by reference in its entirety for all purposes, for the preparation of a tissue extract termed "Cardialin." Approximately 100 milligram (mg) of the resulting bovine heart tissue extract was subjected to preparative scale molecular-sieve chromatography on a 2.6×88 centimeter (cm) G-25 column of superfine resin (Pharmacia/LKB, Sweden) at a flow rate of 1 milliliter/minute (ml/min). Five-milliliter fractions of the column eluent were collected. The absorbance (optical density) of each fraction was measured at 214 and 280 nanometers (nm), respectively. The resulting chromatogram was complex.

Seven pools of fractions were formed for further analysis as follows: a void volume pool (pool I); a center-included volume pool (pool II); a trailing-included volume pool (pool III); and four pools of fractions containing trailing absorbance peaks (pools IV, V, VI, and VII). Components of Pools I, II, and III were evaluated by fast protein liquid chromatography (FPLC) (Pharmacia/LKB, Sweden) employing the Gold-System™ (Kodak) and a 5.0×30 millimeter (mm) column of G-25 superfine resin (Pharmacia/LKB, Sweden). Respective components of these pools were distinguished by comparing elution times, peak areas, and optical density measurements at selected wavelengths. The results are summarized in Table A.

TABLE A

Chromatographic Separation of Cardialin Complex

| Pool No. | Amount of Cardialin* (mg) | Approximate Number of Discrete Absorbance Peaks** |
|---|---|---|
| I | 59.2 | 64 |
| II | 2.1 | 27 |
| III | 1.2 | 19 |
| Total | 62.5 | 110 |

*Estimated from optical density absorbance data assuming an extinction coefficient of ≈ 1.0 $Molar^{-1}centimeter^{-1}$ ($M^{-1}cm^{-1}$).
**Absorbance peaks observed between from 199–214 nm or 249–299 nm.

To identify biologically active components in Pools I to VII from the preparative G-25 superfine resin column, each pool was respectively screened for activation of adenylate cyclase activity in isolated cardiomyocyte cultures by using radioimmunoassay (RIA) as described in "Materials and Methods for the Screening Assay" below. Pools II and V were found to increase significantly the adenylate cyclase activity in cardiomyocytes.

The optical densities of pool II and V were then measured at between 200 nm and 214 nm and at 280 nm. Each pool showed measurable optical densities at the these wavelengths. Because the detection of optical densities at these wavelengths of fractions collected from a molecular-sieve column typically results from the presence of compounds having aromatic residues and peptide bonds, these detection of optical densities for pools II and V suggests that these pools contain compounds having aromatic residues and/or peptide bonds.

To ensure that the biological activity was not due to another component co-eluting with those fractions having optical densities at between 200 nm and 214 nm and at 280 nm, such as a lipid intermediate, Pool II was subjected to addition molecular-sieve chromatography on G-15 superfine resin in the presence of organic solvents. Fractions collected from this column were screened for activation of adenylate cyclase activity. In addition, the optical densities of these fractions were measured at the wavelengths set forth above. As before, the fractions exhibiting activation of adenylate cyclase activity were also found to have measurable optical densities at the above wavelengths.

Pool II was further purified, as above, by FPLC on a 5.0×30 cm G-25 superfine resin column. Eluent fractions were optically monitored from 199 to 214 nm and from 249 to 299 nm. Fractions containing the three major absorbance peaks (termed B1, B2, B3) were further analyzed by high-pressure liquid chromatography (HPLC) using a 4.6×250 mm ODS 18/5 microliter ($\mu$l) column run at 1 ml/min. Elution times and optical densities of the eluent fractions were monitored and used to distinguish at least six major components of Pool II, as summarized in TABLE B below.

TABLE B

Six Major Components of Pool II
Following HPLC Purification

| Component | Elution Time from G-25 SF Column (min) | % Representation of Peak in Pool II | | | Maximum Wavelength(s) of Peak(s) (nm) |
|---|---|---|---|---|---|
| | | B1 | B2 | B3 | |
| 1 | 4.72–4.78 | 4.5 | 1.25 | 35.2 | 199 |
| 2 | 5.03–5.06 | 17.2 | 80.1 | 15.7 | 208 |
| 3 | 6.18–7.06 | 40.8 | 16.6 | 7.5 | 199/250/297 |
| 4 | 7.3–8.25 | ≈1.5 | ≈1.5 | ≈0.9 | 199/265 |
| 5 | 12.07–12.95 | ≈1 | <1 | ≈6 | 199/249 |
| 6 | 13.19–14.11 | <1 | <1 | ≈5 | 199/276 |

Abbreviations:
B1, B2, and B3 = three principal absorbance peaks of fractions collected from fast protein liquid chromatography (FPLC) column; SF = superfine; HPLC = high-pressure liquid chromatography.

Individual ODS 18/51 $\mu$l HPLC peaks were evaluated for activation of adenlyate cyclase activity by using the RIA screening assay followed by additional HPLC seperation in different solvent systems (e.g., acetonitrile), including both isocratic and gradient elution methods. Three closely spaced absorbance peaks (components 1–3 of Table B, above) exhibited the majority of the biological activity, but were relatively inseparable by all techniques employed. The results suggest that one or more peptide complexes were responsible for the observed biological activity of components 1, 2, and 3.

Next, each peak was subjected to Edman degradation. The mole ratios and N-terminal residues of the amino acids detected by this analysis suggested the presence of two dipeptides and two tetrapeptides in the fractions. The mole ratios of the dipeptides suggested that glycine and glutamic acid were present in approximately equal quantities and that valine and threonine were also present in about equal quantities. Based on these findings, the synthetic peptides L-Gly-L-Glu (GE) and L-Val-L-Thr (VT) were prepared and subjected to additional testing for pharmacological activity, as shown in Examples 2 through 9 below.

Materials and Methods for Screening Assay

Cardiomyocytes tolerant to calcium were isolated from rats using the Langendorff perfusion method, a perfusate containing proteolytic enzymes, and mechanical scraping. Cardiomyocytes were isolated and viability evaluated using microscopic morphological criteria, trypan blue exclusion.

The patch-clamp method used to evaluate Cardialin fractions is based on electrophysiological measurements of ion currents moving through individual ion channels in the sarcolemma. Micromanipulation and an inverted microscope were used to implant glass electrodes in and on the membrane of individual cardiomyocytes. By varying the medium composition in the electrode, the ion currents of electrically sensitive potassium channels, including ATP-sensitive Type I and Type II rectification channels, were measured. A background level was established by measuring the outgoing currents for each individual cell prior to adding a substance to be tested (i.e., test substance). With this method, conformational transitions of ion channels from "open" to "closed" states, as reflected in current fluctuations, can be measured. Ion currents were recorded on a magnetograph and then digitally encoded using a PSL-718 interface for processing on an IBM PC/AT computer. A mathematical analysis of the data was conducted using original software. As a positive control substance, the total Cardialin peptide complex was used. In this assay, the Cardialin peptide complex brought about a change in membrane currents within 1 millisecond (ms) at concentrations of $10^{-4}$ to $10^{-2}$ mg/ml of Cardialin, and in the presence of Cardialin, the transition was maintained for up to 3 hours.

The results recorded with Cardialin were as follows. First, following incubation with $10^{-4}$ mg/ml Cardialin for 10 to 15 minutes, a sharp increase in the ion current was observed suggesting that potassium-ion channels were "open" (i.e., in a conducting state), reaching a peak ten-fold higher than the baseline values. Second, at higher Cardialin concentrations (e.g., $10^{-2}$ mg/ml), potassium ion conductivity increased within sixty minutes of incubation of the cardiomyocytes with the peptide complex. Activation of the potassium channel in the presence of $10^{-4}$ mg/ml Cardialin at the exterior surface of the cell was measured by using the following cell-attached configuration: holding millivolts (mV)=+20; temporal sensitivity=0.424 ms; $[K^+]_o$=140 milliMolar (mM) (i.e., the extracellular potassium ion concentration was 140 Mm), and a filter transmission band initially set (that is, over the first 15–20 seconds) for lower frequencies at about 1000 Hertz (Hz), and subsequently set at about 1.5 min to about 300 Hz. Current spikes were recorded over a total of about 220 ms at each time interval. Fifteen to twenty seconds after the addition of Cardialin, maximal recorded currents were about 3 to about 3.5 picoamperes (pA); mean current evoked was about 0.25 pA with current spikes, each having a duration of about 1 to about 3 ms; and total duration of the events was about 17.3 ms (out of the total 220-ms recording time). Approximately 1.5 min after the addition of Cardialin, the maximal recorded current spikes were about 8 pA, each spike having a duration of about 2 to about 4 ms; mean current evoked was about 0.31 pA, and duration of the events recorded was about 8 ms.

The radioimmunoassay for adenylate cyclase activity in cardiomyocytes was conducted according to routine methods in the art.

Example 2

Effects of GE and VT On the Contractile Activity of Rat Portal Vein Smooth Muscle Specimens In this experiment, the effects of GE and VT on spontaneous and potassium chloride-induced contractile activity of a rat portal vein smooth muscle specimen (SMS) sample were compared with those caused by Verapamil, a vasodilator having calcium ion channel blocking activity. The results of this experiment demonstrate that both GE and VT reduce the spontaneous contractile activity of rat portal vein and produce relaxant effects on venous smooth muscle specimens. Furthermore, neither of these dipeptides affects the character of the tonic contraction induced in venous smooth muscles by KCl.

Step 1. Verifying the Suitability of Rat Portal Vein Smooth Muscle Specimens

Rat portal vein SMS samples were surgically isolated from random bred rats weighing 200–250 g. The suitability of each isolated rat portal vein SMS was established by measuring the spontaneous contraction response and its contractile response of the specimen to potassium chloride (KCl) as follows. Each isolated SMS was placed into an organ bath with standard Krebs-Henseleit (KH) solution at 35° C. Then, 0.5 ml of physiological saline were added into the organ bath. In this procedure, one end of the smooth muscle strip was fixed, while the other end of the muscle strip was connected with a probe which transmitted contraction-induced signals to an analog-to-digital converter. The spontaneous contraction curve for each SMS was recorded by taking repeated measurements over a 1-minute period. Next, 0.5 ml of a 600 mM solution of KCl in physiological saline was added to the SMS sample/organ bath to achieve a final concentration of 60 mM KCl. KCl induces contraction of rat portal vein tissue at a fmal tissue concentration of about 60 mM.

The KCl-induced contraction curve for each specimen sample was then recorded over the next 5-minute period. Having determined the values for spontaneous and KCl-induced contraction curves of an SMS sample and confirmed its suitability for use in the experiments, the SMS sample was then washed with standard Krebs-Henseleit solution and stabilized by incubating at 35° C. for 30 minutes. During this stabilization period, the spontaneous contraction curve for each SMS was verified by monitoring the data obtained from analog-to-digital converter.

Step 2. Determining the KCl-Induced Contractile Baseline

A baseline value for the contractile response of a SMS to KCl was determined according to the procedure outlined in Step 1 above. Specifically, each SMS was placed into 0.5 ml of physiological saline in an organ bath at 35° C. The spontaneous contraction curve for each SMS sample was recorded by taking repeated measurements over a 1-minute period. Five milliliters of a 600 mM solution of KCl in physiological saline were then added to each SMS until the fmal concentration of 60 mM KCl was achieved in the bath. Next, the KCl-induced contraction curve for each specimen sample was recorded for 5 minutes. The SMS was washed with standard Krebs-Henseleit solution at 35° C. for 30 minutes. The KCl-induced contraction curve was to serve as a control curve for comparison with the potassium-induced contraction response of the SMS in presence of a test substance or reference substance. GE and VT served as test substances and Verapamil served as the reference substance in this experiment. The General Pharmacology Service Program (Current Test Protocols, PAN Lab, GSP-26) recommends Verapamil as the reference substance in this particular model.

Step 3. Determining the Spontaneous Contraction Baseline

To each SMS in the organ bath prepared according to Steps 2 and 3 above, 0.5 ml of physiological saline was added, and the spontaneous contraction curve was recorded for 1 minute. Each spontaneous contraction curve served as baseline (control) curve for comparison with the respective spontaneous contraction of each SMS in the presence of a test substance or reference substance.

Step 4. Comparison of the Effects of GE, VT, and Verapamil on Spontaneous and Potassium-Induced SMS Contractile Activity The effects of GE, VT, and Verapamil on contractile activity of the SMS were studied as follows. Each SMS was treated with GE, VT, or Verapamil, respectively, by adding 0.5 ml of a solution of the respective substance in physiological saline to the SMS sample/orga bath of Step 3 until a final concentration in the bath of $10^{-6}$ g/ml for GE ($4.9 \times 10^{-6}$ M solution of GE), $10^{-6}$ g/ml for VT ($4.58 \times 10^{-6}$ M solution of VT), or $5 \times 10^{-7}$ g/ml for Verapamil ($1 \times 10^{-6}$ M solution of Verapamil), respectively, was achieved. Spontaneous contraction curve values for each SMS were recorded by making repetitive measurements of the spontaneous contractile activity of each sample at 2, 5, 10, and 15 minutes after the addition of the test or reference substance to each SMS/organ bath. Next, 0.5 ml of a solution of 600 mM solution of KCl in physiologicaorgan bath until a fo each SMS in the organ bath until a final concentration of 60 mM KCl was achieved. The contractile activity of each SMS was then measured for 5 minutes.

Step 5. Calculations

The spontaneous contractile activity of each SMS sample was then evaluated by measuring the contraction amplitude and the area under the contraction curve (AUC) for 1 minute. The values of the parameters after application of GE, VT and Verapamil were expressed as percentage of corresponding baseline (control) value established in Step 3. The results are presented in Tables 1 and 2.

Tonic (potassium-induced) contractile activity was determined by calculating the area under the contraction curve for 1 minute. The parameter values after application of GE, VT and Verapamil were expressed as percentage of corresponding baseline (control) value established for potassium-induced contraction in Step 2. The results are presented in Table 3. For each test or reference substance, determinations were made on 5 isolated SMS samples. All results are presented as mean values with standard deviation.

TABLE 1

The Effects of GE and VT on Spontaneous Activity of Smooth Muscle Cells of Rat Portal Vein

| | | Amplitude of Contraction (% of Control) | | | |
|---|---|---|---|---|---|
| | | Minutes After Application Substance | | | |
| Substance | Control (S) | 2 min | 5 min | 10 min | 15 min |
| GE | 100.00 | 114.93 (±14.62) | 75.56 (±12.13) | 60.37 (±12.46)* | 63.94 (±11.78)* |
| VT | 100.00 | 89.24 (±7.71) | 51.79 (±5.42)* | 36.34 (±4.43)* | 39.11 (±5.98)* |
| Verapamil | 100.00 | 95.82 (±19.44) | 78.58 (±22.20) | 60.79 (±11.50)* | 37.92 (±11.08)* |

*Significantly different (P < 0.05, paired Student's t-test) from control level (100%).
Abbreviation: S = Physiological saline.

TABLE 2

The Effects of GE and VT on Spontaneous Activity of Smooth Muscle Cells of Rat Portal Vein Area Under Curve (% of Control)

| Substance | Control (S) | 2 min | 5 min | 10 min | 15 min |
|---|---|---|---|---|---|
| GE | 100.00 | 134.77 (±15.51) | 87.51 (±10.97) | 70.07 (±15.34) | 75.08 (±12.94) |
| VT | 100.00 | 139.92 (±6.25)* | 59.08 (±12.25)* | 45.93 (±6.91)* | 36.35 (±2.30)* |
| Verapamil | 100.00 | 82.41 (±18.92) | 62.11 (±14.06) | 49.83 (±8.86)* | 35.13 (±11.95)* |

Minutes After Application of Substance

*Significantly different (P < 0.05, paired Student's t-test) from control level (100%).
Abbreviation: S = Physiological saline.

TABLE 3

The Effects of GE and VT on Tonic Contraction of Rat Portal Vein Induced by KCl
Area Under Curve of KCl-Induced Contraction (% of control)

| Substance | Control KCl Application | % Control (by test or reference substance) |
|---|---|---|
| GE | 100.00 | 90.26 (±5.05) |
| VT | 100.00 | 93.46 (±4.01) |
| Verapamil | 100.00 | 23.98 (±6.98)* |

*Significantly different (P < 0.05, paired Student's t-test) from control level (100%).

As shown in Tables 1 and 2, both GE and VT appreciably reduced the amplitude of and area under the contraction curve for spontaneous contractions exhibited in organ culture by isolated venous smooth muscle specimens. It is noteworthy that the rate of VT-induced effect onset was more rapid as compared with Verapamil. The results presented in Tables 1 and 2 demonstrate that GE and VT had relaxant effects on the smooth muscle of vessels in organ culture.

Furthermore, although GE and VT reduced spontaneous contraction, neither GE nor VT effected the character of the tonic contraction induced in venous smooth muscle specimens by KCl, as shown in Table 3. These results are in contrast with those observed with Verapamil, which had a pronounced effect on tonic contraction induced by KCl.

Substances having potassium channel activity are known to reduce spontaneous contractile activity, but not potassium-induced contraction activity, in vascular smooth muscle specimens. Nidel et al., *Br. J. Pharm.* 95: 741–52 (1988). The results of this experiment suggest that GE and VT have potassium channel activity because they both reduce spontaneous contractile activity, but not potassium-induced tonic contraction activity.

Example 3

Effects of GE and VT on Calcium-Induced Contractile Activity of Intestinal Smooth Muscle Specimen Samples In this experiment, the effects of GE and VT on calcium-induced contractile activity of intestinal smooth muscle specimen samples were investigated. The results of this experiment show that GE and VT decrease the amplitude of calcium-induced smooth muscle tonic contraction and induce relaxation of smooth muscle.

GE and VT served as test substances in this experiment. GE was tested at concentrations of $10^{-6}$ g/ml and $10^{-5}$ g/ml ($4.9 \times 10^{-6}$M and $4.9 \times 10^{-5}$M, respectively), and VT was tested at concentrations $10^{-6}$ g/ml and $10^{-5}$ g/ml ($4.58 \times 10^{-6}$ and $4.58 \times 10^{-5}$M, respectively). The calcium ion channel blockers Verapamil, cholinolytic atropine, and diltiazem served as reference substances and were tested at the following concentrations: $10^{-8}$ g/ml and $10^{-7}$ g/ml Verapamil ($2.04 \times 10^{-8}$M and $2.04 \times 10^{-7}$M, respectively); $10^{-6}$ g/ml and $10^{-7}$ g/ml cholinolytic atropine ($1.48 \times 10^{-7}$M and $1.48 \times 10^{-6}$M, respectively); and $10^{-9}$ g/ml and $10^{-8}$ g/ml diltiazem ($2.2 \times 10^{-9}$M and $2.2 \times 10^{-8}$M, respectively).

Step 1. Specimen Preparation

Small intestinal SMS samples from ten guinea pigs were surgically isolated and prepared as follows. First, the SMS samples were preincubated for 40 minutes in an organ bath holding a standard Krebs-Henseleit physiological salt solution containing calcium chloride ($CaCl_2$) at concentration of 2.5 mM. Next, each SMS was washed with a calcium-free solution of Krebs-Henseleit and incubated in a calcium-free Krebs-Henseleit solution for 40 minutes. Contractile activity was pre-induced in each SMS by first perfusing the organ bath containing the sample for 15 minutes with a Krebs-Henseleit solution containing 30 mM KCl and then perfusing the bath for an additional 15 minutes with a Krebs-Henseleit solution containing 20 mM $CaCl_2$. Finally, each SMS sample was washed with a calcium-free Krebs-Henseleit solution for 40 minutes. In these experiments, measurements of the contractile response of the SMS following the addition of a Krebs-Henseleit solution containing 20 mM calcium served as the control (baseline). Changes in contraction amplitudes were recorded by using the method set forth in Step 1 of Example 2, above.

Step 2. Application I

After washing the SMS as outlined in Step 1, the organ bath with the SMS sample was perfused for 15 minutes with the solution of a test or reference substance. In this instance, GE and VT served as the test substances, and each dipeptide was tested at a concentration of $10^{-6}$ g/ml. The following reference substances were employed: $10^{-8}$ g/ml Verapamil, $10^{-7}$ g/ml cholinolytic atropine, and $10^{-9}$ g/ml diltiazem.

Following perfusion with the test or reference substance, the SMS sample/organ bath was perfused for 10 minutes with a Krebs-Henseleit solution containing 30 mM KCl and then perfused for an additional 10 minutes with a Krebs-Henseleit solution containing 20 mM $CaCl_2$. Next, each SMS sample was washed with a calcium-free Krebs-Henseleit solution for 40 minutes. The effect of the test or reference substance on the SMS sample was evaluated by measuring the contractile response (i.e., the change in contraction amplitude) of the sample following the addition of the Krebs-Henseleit solution containing 20 mM $CaCl_2$.

Step 3. Application II

Each SMS from Step 2 was exposed a second time to the same test or reference substance by adding the following concentration of each respective reference or test substance to the perfusate of the organ bath: $10^{-7}$ g/ml Verapamil; $10^{-6}$ g/ml cholinolytic atropine; $10^{-8}$ g/ml diltiazem; and either $10^{-5}$ g/ml GE or $10^{-5}$ g/ml VT.

Next, the organ bath was perfused for 10 minutes with a Krebs-Henseleit solution containing 30 mM KCl and then for additional 10 minutes with a Krebs-Henseleit solution containing 20 mM $CaCl_2$. The effect of the respective test or reference substance was evaluated a second time by measuring the change in the contraction amplitude of the SMS following the addition of the Krebs-Henseleit solution containing 20 mM $CaCl_2$. The cardiac work efficiency was evaluated by determining the area under the contraction curve of an isolated smooth muscle specimen.

As the results in Table 4 demonstrate, both GE and VT significantly reduced the amplitude of calcium-induced intestinal smooth muscle tonic contraction. Notably, the effect of VT was greater than observed for the standard calcium ion channel blockers Verapamil and diltiazem.

TABLE 4

The Effects of GE and VT on Amplitude of Calcium-Induced Contraction of Intestinal Smooth Muscle

| Substance | Control (%, KH) | Contraction Amplitude (% of control[a] level) | |
|---|---|---|---|
| | | Application I | Application II |
| Atropine | 100.00 | 39.57* (±13.52) | 25.08* (±6.20) |
| Diltiazem | 100.00 | 39.02* (±11.78) | 12.95* (±7.82) |
| Verapamil | 100.00 | 39.57* (±13.52) | 25.08* (±6.20) |
| GE | 100.00 | 51.08* (±14.13) | 33.14* (±15.59) |
| VT | 100.00 | 26.58* (±9.33)* | 11.51* (±7.27)* |

*Significantly different (P < 0.05, Student's t-test) from control level (100%).
[a]% of control, where control values were taken after application of a Krebs-Henseleit solution containing 20 mM calcium as described in Step 1 of Example 3.
Abbreviations: KH = Krebs-Henseleit.

Example 4.1

Effects of GE and VT on the Inotropic Function of a Normal Rat Heart

This experiment was designed to evaluate the respective effects of GE and VT on the inotropic function of an isolated rat heart. The inotropic function of the heart was evaluated by measuring various parameters, including the systolic pressure in the left ventricle ($P_{syst.}$ mm Hg); the diastolic pressure in the left ventricle ($P_{diast.}$ mm Hg); (iii) the evolving pressure ($P_{ev.} = P_{syst.} - P_{diast.}$ mm Hg); (iv) the maximal rate of increase of left ventricle pressure ($+dp/dt_{max}$ mm Hg/sec); and (v) the maximal rate of decrease of left ventricle pressure ($-dp/dt_{max}$ mm Hg/sec). In addition, the heart rate (HR) of each heart was determined from the pressure variation recordings made of the left ventricle pressure. This experiment demonstrates that neither GE nor VT has a significant effect on the inotropic function or on the heart rate of a normal heart.

Rat heart specimens were obtained surgically from white random-bred male rats weighing approximately 250 g. The hearts were established in culture using retrograde heart perfusion according to the Langendorff method performed with a standard oxygenated (95% $O_2$ and 5% $CO_2$) Krebs-Henseleit solution through a glass aorta cannula. The retroperfusion pressure forces the aortic valves shut. In this way, the oxygenated solution passed only through the coronary vasculature of the heart such that both ventricles remain effectively empty.

Perfusion conditions: An average constant perfusate flow rate of 15 to 25 ml/min was maintained with a constant perfusate pressure of 80 cm $H_2O$.

Pressure Measurements: A latex balloon catheter connected with a pressure transducer (EMT-746 Siemens-Elema, Sweden) was inserted into the left ventricle of the heart to measure parameters of the inotropic function of the heart. The intraventricle pressure variation curve for the left ventricle was recorded with a polygraph.

Experimental Protocol: GE and VT served as the test substances. After a 30-minute adaptation of the heart to the organ culture perfusion conditions, a set of basal (control) measurements was taken, as described in (i) through (v) below. Following these measurements, GE or VT was introduced into the perfusate flow at a dose of 10, 100, or 1000 μg per 0.1 ml Krebs-Henseleit solution. The sympathomimetic amine, isoproterenol (Novodrin, Germed, Germany), served as the reference substance and was administered at a dose of 0.01 mg. Isoproterenol is known to lower peripheral vascular resistance and raise cardiac output because of its positive inotropic (i.e., increasing the efficiency of contractile work performed by an ischemic heart) and chronotropic actions when infused into a subject intravenously. See GOODMAN AND GILMAN'S THE PHARMACOLOGICAL BASIS OF THERAPEUTICS 160 (Goodman et al., eds., 7th ed. 1985), incorporated herein by reference in its entirety for all purposes. Each dose of each respective test or reference substance was tested on four different rat hearts. The inotropic functions of each of the four rat hearts were evaluated by measuring: (i) the systolic pressure in the left ventricle ($P_{syst.}$ mm Hg); (ii) the diastolic pressure in the left ventricle ($P_{diast.}$ mm Hg); (iii) the evolving pressure ($P_{ev.} = P_{syst.} - P_{diast.}$ mm Hg); (iv) the maximal rate of increase of left ventricle pressure ($+dp/dt_{max}$ mm Hg/sec); and (v) the maximal rate of decrease of left ventricle pressure ($-dp/dt_{max}$ mm Hg/sec). In addition, the heart rate (HR) of each heart was determined from the pressure variation recordings made of the left ventricle pressure.

As shown by the results presented in Tables 5A and 5B, neither GE nor VT had a significant effect on the inotropic function or the heart rate of the heart. Rather, each dipeptide had little or a minimal effect on these parameters.

TABLE 5A

The Effect of GE on Work of Isolated Rat Heart Perfused Using Langendorff Perfusion Method (Mean of Measurements)

| | | HR | | | $P_{syst}$ | | | $P_{diast}$ | | |
|---|---|---|---|---|---|---|---|---|---|---|
| | | abs (hb/min) | | % of | abs (mm Hg) | | % of | abs (mm Hg) | | % of |
| Substance | Dose (mg) | Basal Level | Subst. Level | Basal Level | Basal Level | Subst. Level | Basal Level | Basal Level | Subst. Level | Basal Level |
| Isoproterenol | 0.01 | 192 (±56) | 255 (±13) | 133 (±4)* | 101 (±4) | 119 (±6) | 117 (±1)* | 10 (±1) | 12 (±1) | 120 (±4)* |
| GE | 10 | 205 (±10) | 202 (±8) | 99 (±2) | 102 (±3) | 104 (±4) | 102 (±2) | 10 (±1) | 9 (±1) | 95 (±2) |
| | 100 | 203 (±11) | 203 (±14) | 100 (±2) | 101 (±1) | 99 (±1) | 99 (±1) | 11 (±1) | 11 (±1) | 100 (±4) |

TABLE 5A-continued

The Effect of GE on Work of Isolated Rat Heart Perfused Using
Langendorff Perfusion Method (Mean of Measurements)

| | 1000 | 196 | 198 | 102 | 103 | 94 | 92 | 10 | 10 | 100 |
|---|---|---|---|---|---|---|---|---|---|---|
| | | (±11) | (±12) | (±2) | (±3) | (±4) | (±2) | (±1) | (±1) | (±5) |

| | | $P_{ev}$ | | % of | $+dp/dt_{max}$ | | % of | $-dp/dt_{max}$ | | |
|---|---|---|---|---|---|---|---|---|---|---|
| Substance | Dose (mg) | Basal Level | Subst. Level | Basal Level | Basal Level | Subst. Level | Basal Level | Basal Level | Subst. Level | Basal Level |
| Isoproterenol | 0.01 | 91 | 108 | 118 | 1728 | 2110 | 122 | 1023 | 1140 | 112 |
| | | (±3) | (±8) | (±5)* | (±32) | (±87) | (±3)* | (±27) | (±17) | (±3)* |
| GE | 10 | 92 | 94 | 102 | 1723 | 1750 | 102 | 1045 | 985 | 94 |
| | | (±4) | (±3) | (±3) | (±36) | (±104) | (±6) | (±56) | (±56) | (±4) |
| | 100 | 90 | 88 | 99 | 1720 | 1723 | 100 | 1070 | 1055 | 99 |
| | | (±2) | (±1) | (±1) | (±34) | (±34) | (±1) | (±30) | (±46) | (±1) |
| | 1000 | 94 | 85 | 91 | 1713 | 1618 | 94 | 1023 | 980 | 96 |
| | | (±4) | (±4) | (±1) | (±19) | (±80) | (±4) | (±34) | (±34) | (±2) |

*Significantly different ($P < 0.05$, Student's t-test) from basal (control) level.
Abbreviations: mg = microgram; Subst. = substance; abs = absolute value; HR = heart rate; hb/min = heart beats/minute; $P_{syst.}$ = systolic pressure in left ventricle; $P_{diast.}$ = diastolic pressure in left ventricle; $P_{ev}$ = evolving pressure; $+dp/dt_{max}$ = maximal rate of increase of left ventricle pressure; $-dp/dt_{max}$ = maximal rate of decrease of left ventricle pressure.

TABLE 5B

The Effect of VT on Work of Isolated Rat Heart Perfused Using
Langendorff Perfusion Method (Mean of Value)

| | | HR | | | $P_{syst}$ | | | $P_{diast}$ | | |
|---|---|---|---|---|---|---|---|---|---|---|
| | | abs (hb/min) | | % of | abs (mm Hg) | | % of | abs (mm Hg) | | % of |
| Substance | Dose (mg) | Basal Level | Subst. Level | Basal Level | Basal Level | Subst. Level | Basal Level | Basal Level | Subst. Level | Basal Level |
| Isoproterenol | 0.01 | 192 | 255 | 133 | 101 | 119 | 117 | 10 | 12 | 120 |
| | | (±56) | (±13) | (±4)* | (±4) | (±6) | (±1)* | (±1) | (±1) | (±4)* |
| VT | 10 | 199 | 199 | 100 | 102 | 103 | 102 | 10 | 10 | 100 |
| | | (±9) | (±8) | (±1) | (±3) | (±3) | (±1) | (±1) | (±1) | (±4) |
| | 100 | 191 | 914 | 102 | 103 | 108 | 106 | 10 | 10 | 100 |
| | | (±16) | (±18) | (±2) | (±2) | (±2) | (±4) | (±1) | (±1) | (±5) |
| | 1000 | 194 | 195 | 101 | 100 | 102 | 102 | 10 | 10 | 100 |
| | | (±10) | (±8) | (±2) | (±3) | (±8) | (±4) | (±1) | (±1) | (±2) |

| | | $P_{ev}$ | | % of | $+dp/dt_{max}$ | | % of | $-dp/dt_{max}$ | | |
|---|---|---|---|---|---|---|---|---|---|---|
| Substance | Dose (mg) | Basal Level | Subst. Level | Basal Level | Basal Level | Subst. Level | Basal Level | Basal Level | Subst. Level | Basal Level |
| Isoproterenol | 0.01 | 91 | 108 | 118 | 1728 | 2110 | 122 | 1023 | 1140 | 112 |
| | | (±3) | (±8) | (±5)* | (±32) | (±87) | (±3)* | (±27) | (±17) | (±3)* |
| VT | 10 | 92 | 93 | 101 | 1745 | 1788 | 103 | 1035 | 1045 | 101 |
| | | (±2) | (±2) | (±1) | (±29) | (±58) | (±1) | (±56) | (±56) | (±1) |
| | 100 | 93 | 98 | 105 | 1713 | 1789 | 105 | 1123 | 1198 | 107 |
| | | (±2) | (±2) | (±4) | (±24) | (±141) | (±9) | (±56) | (±92) | (±4) |
| | 1000 | 90 | 91 | 102 | 1753 | 1783 | 102 | 1015 | 1055 | 104 |
| | | (±3) | (±7) | (±4) | (±24) | (±9) | (±4) | (±19) | (±7) | (±2) |

*Significantly different ($P < 0.05$, Student's t-test) from basal (control) level.
Abbreviations: mg = microgram; Subst. = substance; abs = absolute value; HR = heart rate; hb/min = heart beats/minute; $P_{syst.}$ = systolic pressure in left ventricle; $P_{diast.}$ = diastolic pressure in left ventricle; $P_{ev}$ = evolving pressure; $+dp/dt_{max}$ = maximal rate of increase of left ventricle pressure; $-dp/dt_{max}$ = maximal rate of decrease of left ventricle pressure.

Example 4.2

Effects of GE and VT on Inotropic Function of Ischemic Myocardium

In this experiment, the effects of GE and VT on the inotropic function of ischemic myocardial tissue were evaluated by measuring various parameters of the inotropic function of the heart. The results of this experiment reveal that each of these dipeptides restores the inotropic function of myocardial tissue in which ischemia has been induced and reduces the effects of ischemic damage in myocardial tissue.

Rat hearts were surgically isolated from white random-bred rats weighing approximately 250 g. The isolated hearts were perfused with a standard oxygenated (95% $O_2$ and 5% $CO2$) Krebs-Henseleit solution in a retrograde manner (i.e., according to Langendorff and using a constant perfusate pressure of 80 cm of water). The hearts maintained a steady spontaneous contraction rate. A latex balloon catheter connected to a pressure transducer (EMT-746, Siemens-Elema, Sweden) was inserted into the left ventricle of each heart to measure the inotropic function of the heart (as described in Example 3, above). The left ventricle pressure variation curve was recorded using a polygraph.

Experimental Protocol:

Stage I ("adaptation regimen") consisted of a 30-minute adaptation of the respective rat hearts to the perfusion regimen. The baseline parameters for the inotropic function of each heart were recorded to establish the preischemic values for the following measured parameters: (i) the systolic pressure in the left ventricle ($P_{syst.}$ mm Hg); (ii) the diastolic pressure in the left ventricle ($P_{diast.}$ mm Hg); (iii) the evolving pressure ($P_{ev.}=P_{syst.}-P_{dist.}$ mm Hg); (iv) the maximal rate of increase of left ventricle pressure ($+dp/dt_{max}$ mm Hg/sec); and (v) the maximal rate of decrease of left ventricle pressure ($-dp/dt_{max}$ mm Hg/sec). In addition, the heart rate (HR) of each heart was determined from the recordings made of the variations in the left ventricle pressure over time. In Stage II ("ischemic simulation"), ischemia was induced in each heart by shutting off the supply of the perfusion solution to the heart. Approximately 30 minutes later, Stage III ("reperfusion regimen") was initiated by restarting the reperfusion and including in the perfusate solution a test or control substance at one of the following respective concentrations: a perfusate solution of a test substance comprised 0.06, 0.6, or 6.0 mg/l GE, or 0.06, 0.6, or 6.0 mg/l VT, respectively; a perfusate solution of the positive control substance comprised 14 mg/l inosine. Inosine is a nucleoside preparation that produces a favorable inotropic effect on both normal and ischemic myocardium while inducing no rhythm disturbances or acceleration of ischemic contracture development. Woollard et al., *Cardiovasc. Res.* 15: 659–67 (1981). Inosine was obtained from Sigma Chemical Company, USA (Cat. Code I-4125; lot number 81H0227). The negative control substance comprised reperfusion using a standard oxygenated Krebs-Henseleit solution.

For each heart, the inotropic function of the myocardium was evaluated by measuring the parameters (i) through (v), discussed above, and the heart rate. These six parameters were recorded continuously throughout the study (i.e., beginning with Stage I and continuing through Stage III). The recordings were analyzed at the following times: (a) immediately before beginning Stage II (that is, after the 30-minute Stage I adaptation period, but before stopping perfusion); and (b) at 1, 5, 10, 20, and 30 minutes into the Stage III reperfusion.

The frequency and duration of rhythm disturbances in the 30-minute Stage III reperfusion period were determined by measuring the following parameters: (i) the number of ventricular extrasystoles; (ii) the overall duration of ventricular tachycardias (in seconds); and (iii) the overall duration of ventricular fibrillation (in seconds). Each dose of the test substance was tested on nine isolated hearts.

The results of this study are presented in Tables 6 through 12 below. As shown in Table 6, induction of ischemia in this heart model resulted in an approximately 50% reduction in systolic pressure at 1 minute after initiation of the Stage III reperfusion (the negative control). Although some recovery in systolic pressure in the negative control was observed at 5 to 10 minutes (i.e, recovery to about 78% of the preischemic systolic pressure), the pressure deteriorated thereafter. Reperfusion with GE or VT at concentrations of 0.06 and 0.6 mg/l, respectively, prevented the dramatic drop in systolic pressure observed in the negative control. The effects of GE and VT were more pronounced and more rapidly expressed in this model than were the effects of inosine, which caused a gradual improvement in systolic pressure during the 30-minute observation period.

TABLE 6

The Effects of GE and VT on Systolic Pressure in an Ischemic Left Ventricle During Reperfusion (% of Preischemic Parameter Values)

| Substance | Dose (mg/l) | Reperfusion | | | | |
|---|---|---|---|---|---|---|
| | | 1 min | 5 min | 10 min | 20 min | 30 min |
| Negative control | — | 49.39 | 76.75 | 77.54 | 62.03 | 58.03 |
| GE | 0.06 | 115.11* | 98.86 | 89.79 | 84.10 | 72.11 |
| | 0.6 | 74.01 | 90.02 | 88.40 | 82.35 | 91.89* |
| | 6.0 | 72.87 | 67.10 | 77.71 | 77.71 | 79.73 |
| VT | 0.06 | 91.69 | 94.33 | 82.56 | 85.55 | 79.52 |
| | 0.6 | 128.62* | 99.34 | 102.23 | 89.31 | 88.47* |
| | 6.0 | 102.32 | 74.59 | 77.58 | 69.85 | 65.28 |
| Inosine | 14.0 | 62.15 | 66.17 | 86.05 | 99.29* | 96.62 |

*Significantly different (P < 0.05, Student's t-test) from corresponding negative control group values.

Measurements of the maximal rate of increase of the pressure of ischemic left ventricles ($+dp/dt_{max}$) of rat hearts are summarized in Table 7. Induction of ischemia in this heart model resulted in an approximately 46% reduction in the $+dp/dt_{max}$ value of the negative control at 1 minute after initiation of reperfusion. While recovery of the $+dp/dt_{max}$ in the negative control to about 82% of its preischemic value was observed after 5 minutes, the $+dp/dt_{max}$ deteriorated subsequently. GE and VT were found to increase $+dp/dt_{max}$ value during the first minute of reperfusion. Notably, concentrations of 0.6 mg/l GE and VT, respectively, were found to restore $+dp/dt_{max}$ of an isolated heart nearly to its preischemic level after 30 minutes of reperfusion.

TABLE 7

The Effects of GE and VT on Maximal Rate of Increase of Left Ventricle Pressure During Reperfusion (% of Preischemic Parameter Mean Value)

| Substance | Dose (mg/l) | Reperfusion | | | | |
|---|---|---|---|---|---|---|
| | | 1 min | 5 min | 10 min | 20 min | 30 min |
| Negative control | — | 46.47 | 81.84 | 73.74 | 54.75 | 40.02 |
| GE | 0.06 | 127.30* | 98.87 | 87.39 | 87.39 | 70.93 |
| | 0.6 | 71.21 | 84.14 | 88.69 | 81.12 | 97.62* |
| | 6.0 | 71.18 | 68.10 | 77.78 | 82.47 | 74.49 |
| VT | 0.06 | 93.83 | 89.14 | 76.40 | 80.01 | 70.75 |
| | 0.6 | 118.03* | 89.62 | 93.64 | 85.26 | 85.51* |
| | 6.0 | 101.78 | 71.53 | 62.09 | 67.53 | 57.96 |
| Inosine | 14.0 | 50.85 | 54.25 | 82.35 | 83.58* | 77.85 |

*Significantly different (P < 0.05, Student's t-test) from corresponding negative control group values.

The effects of various concentrations of GE and VT on the diastolic pressure of this rat heart model are presented in Table 8. Following the induction of ischemia in this model, diastolic pressure in the left ventricle increased by more than two-fold in the negative control. Both GE and VT prevented the increase in diastolic pressure and were found to be at least as effective as inosine in this model.

TABLE 8

The Effects of GE and VT on Diastolic Pressure in an Ischemic Left Ventricle During Reperfusion (% of Preischemic Parameter Mean Value)

| Substance | Dose (mg/l) | Reperfusion | | | | |
|---|---|---|---|---|---|---|
| | | 1 min | 5 min | 10 min | 20 min | 30 min |
| Negative control | — | 228.69 | 287.43 | 233.32 | 175.24 | 212.68 |
| GE | 0.06 | 95.96 | 124.53 | 128.57 | 134.92 | 91.20 |
| | 0.6 | 69.70 | 113.42 | 95.24 | 99.28 | 127.06 |
| | 6.0 | 53.97 | 65.08 | 103.17 | 83.98 | 132.47 |
| VT | 0.06 | 112.41 | 98.27 | 118.76 | 115.44 | 112.41 |
| | 0.6 | 101.59 | 97.55 | 115.01 | 115.01 | 115.01 |
| | 6.0 | 96.61 | 173.67 | 213.35 | 169.62 | 151.44 |
| Insoine | 14.0 | 92.35 | 111.83 | 139.32 | 148.63 | 149.42 |

Measurements of the maximal rate of the decrease of left ventricle pressure ($-dp/dt_{max}$) in ischemic left ventricles of rat hearts are summarized in Table 9. These results show an approximately 50% reduction in the $-dp/dt_{max}$ value in an ischemic left ventricle for the negative control at 1 minute after initiation of the Stage III reperfusion (the negative control). Although the parameter $-dp/dt_{max}$ for the negative control recovered to about 88% of its preischemic value after about 10 minutes, $-dp/dt_{max}$ decreased thereafter. In this model, GE and VT were each observed to increase significantly the $-dp/dt_{max}$ value in the ischemic left ventricle within the first minute of reperfusion; for example, the parameter mean value increased to about 80 to 100% of its preischemic value with 0.06 mg/l GE, 0.06 mg/l VT, and 0.6 mg/l VT, respectively. At the later times, $-dp/dt_{max}$ for a heart treated with 0.6 mg/l GE, 6.0 mg/l GE, or 0.6 mg/l VT, respectively, was typically higher than that observed for the negative control, and by the 30th minute of reperfusion, was greater than about 90% of its preischemic value. Reperfusion with inosine (the positive control substance) produced a slow, steady increase in the $-dp/dt_{max}$ in a heart such that about 80% of the preischemic value for the parameter was achieved after approximately 10 to 20 minutes.

TABLE 9

The Effects of GE and VT on Maximal Rate of Left Ventricle Pressure Decrease During Reperfusion (% of Preischemic Parameter Mean Value)

| Substance | Dose (mg/l) | Reperfusion | | | | |
|---|---|---|---|---|---|---|
| | | 1 min | 5 min | 10 min | 20 min | 30 min |
| Negative control | — | 48.74 | 75.90 | 87.57 | 80.59 | 75.17 |
| GE | 0.06 | 86.91* | 89.27 | 82.04 | 75.11 | 66.02 |
| | 0.6 | 53.56 | 79.56 | 87.20 | 84.10 | 91.20 |
| | 6.0 | 59.93 | 70.76 | 93.15 | 95.32 | 93.07 |
| VT | 0.06 | 80.75 | 83.92 | 77.75 | 84.23 | 76.22 |
| | 0.6 | 100.31* | 85.83 | 96.20 | 88.18 | 91.44 |
| | 6.0 | 75.83 | 65.42 | 70.90 | 69.93 | 60.00 |
| Inosine | 14.0 | 41.91 | 65.94 | 78.85 | 91.83 | 93.88 |

*Significantly different (P < 0.05, Student's t-test) from corresponding negative control group values.

The evolving pressure of the heart is an important parameter reflecting the inotropic pumping function of the heart. The results presented in Table 10 show that following induction of ischemia in the left ventricle of a rat heart, the evolving pressure decreased to approximately 29% of its preischemic value within 1 minute and never exceeded about 55% of its preischemic value during the subsequent 30-minute observation period. Reperfusion with GE and VT increased measured evolving pressure values to within about 70 to 100% of their respective preischemic values. Reperfusion with either 0.6 mg/l GE or 0.6 mg/l VT was found to restore the evolving pressure value of an ischemic left ventricle to about 85% or greater of its respective preischemic level after about 20 or about 30 minutes of reperfusion, respectively.

TABLE 10

The Effects of GE and VT on Evolving Pressure in an Ischemic Left Ventricle During Reperfusion (% of Preischemic Parameter Mean Value)

| Substance | Dose (mg/l) | Reperfusion | | | | |
|---|---|---|---|---|---|---|
| | | 1 min | 5 min | 10 min | 20 min | 30 min |
| Negative control | — | 29.04 | 51.50 | 55.16 | 45.39 | 34.17 |
| GE | 0.06 | 117.70* | 92.58* | 86.19 | 74.40 | 68.73 |
| | 0.6 | 71.90 | 83.73 | 86.63 | 78.42* | 87.22* |
| | 6.0 | 78.34 | 68.80 | 74.86 | 78.47 | 73.08* |
| VT | 0.06 | 90.10* | 93.41 | 74.75 | 78.47 | 71.47 |
| | 0.6 | 136.04* | 101.11 | 101.53* | 86.21* | 84.99* |
| | 6.0 | 99.46 | 67.93 | 63.87 | 57.45 | 55.34 |
| Inosine | 14.0 | 57.13 | 57.59 | 82.33 | 94.19 | 91.68* |

*Significantly different (P < 0.05, Student's t-test) from corresponding negative control group values.

The effects of GE and VT on the heart rate of this rat heart model are presented in Table 11. GE and VT each produced a desirable moderate negative chronotropic effect on heart rate (i.e., a decrease in heart rate) at concentrations of 0.06 and 6.0 mg/l.

TABLE 11

The Effects of GE and VT on Heart Rate Reperfusion (% of Preischemic Parameter Mean Value)

| Substance | Dose (mg/l) | Reperfusion | | | | |
|---|---|---|---|---|---|---|
| | | 1 min | 5 min | 10 min | 20 min | 30 min |
| Negative control | — | 51.98 | 71.35 | 91.57 | 108.51 | 109.30 |
| GE | 0.06 | 69.09 | 91.94 | 93.44 | 72.87* | 68.67* |
| | 0.6 | 52.28 | 85.30 | 77.07 | 91.53 | 106.61 |
| | 6.0 | 38.86 | 55.65 | 82.12 | 77.12* | 63.29 |
| VT | 0.06 | 92.58 | 65.90 | 72.02 | 83.84 | 82.52 |
| | 0.6 | 71.30 | 91.90 | 113.52 | 108.41 | 101/74 |
| | 6.0 | 59.54 | 71.39 | 75.19 | 103.33 | 82.04 |
| Inosine | 14.0 | 45.37 | 69.97 | 67.52 | 79.97* | 75.60* |

*Significantly different (P < 0.05, Student's t-test) from corresponding negative control group values.

Table 12 shows the effects of GE and VT on the frequency and duration of ventricular arrhythmias during reperfusion. Neither GE nor VT was found to have an arrhythmogenic effect on the rat heart model employed in this study.

TABLE 12

The Effects of GE and VT on Frequency and Duration of Ventricular Arrhythmias During Reperfusion

| Substance | Concentration (mg/l) | Number of Ventricular Extrasystoles | Overall Duration of Ventricular Tachycardia (sec) | Overall Duration of Ventricular Fibrillation (sec) |
|---|---|---|---|---|
| Negative control | — | 180 (±41.48) | 10.2 (±9.48) | 32.1 (±28.55) |
| GE | 0.06 | 182.2 | 2.1 | 0 |

TABLE 12-continued

The Effects of GE and VT on Frequency and Duration of Ventricular Arrhythmias During Reperfusion

| Substance | Concentration (mg/l) | Number of Ventricular Extrasystoles | Overall Duration of Ventricular Tachycardia (sec) | Overall Duration of Ventricular Fibrillation (sec) |
|---|---|---|---|---|
| | | (±54.50) | (±1.26) | |
| | 0.6 | 168.5 | 22.2 | 44.3 |
| | | (±54.50) | (±21.60) | (±30.37) |
| | 6.0 | 174.9 | 5.2 | 79.6 |
| | | (±34.50) | (±2.63) | (±38.24) |
| VT | 0.06 | 154.5 | 7.7 | 29.3 |
| | | (±20.85) | (±3.63) | (±29.33) |
| | 0.6 | 182.4 | 4.4 | 35.1 |
| | | (±20.85) | (±3.56) | (±29.33) |
| | 6.0 | 104.4 | 0 | 0 |
| | | (±20.82) | | |
| Inosine | 14.1 | 230.4 | 1.3 | 52.9 |
| | | (±41.39) | (±0.94) | (±52.90) |

*Significantly different (P < 0.05, Student's t-test) from corresponding negative control group values.

In summary, GE and VT were found to optimize the inotropic function of the heart during ischemia as shown by improvements in the measured values for the systolic pressure, evolving pressure, and the maximal rate of increase of left ventricle pressure (+dp/dt$_{max}$) in the rat test hearts. GE and VT also prevented the development of ischemic contractures and produced no arrhythmogenic effect on ischemic myocardium. These observed effects are consistent with those induced by pharmaceutical compounds having potassium channel opener activity.

Example 5

Effects of GE and VT on Myocardial Ischemic Lesions in Animals

Coronary artery ligation leads to acute myocardial ischemia with irreversible lesions in cardiomyocyte membranes and the release of intracellular myocardial enzymes, including creatinine phosphokinase (CPK), into the blood. The level of the enzymatic activity of CPK in plasma during the first hours of ischemia has been correlated with the extent of the myocardial ischemic lesion. See, e.g., G. Forster et al., Method of Enzymatic Analysis (U. Bergmeyer and W. Weynhame, eds., Verlack Chemie GMBH). In this experiment, CPK activity was measured to monitor the extent of myocardial ischemic damage resulting from coronary artery occlusion by ligation. Specifically, CPK activity was measured at 1 hour following coronary artery occlusion in rats that remained untreated or, alternatively, were treated with an intravenous injection of a test or control substance. The results of this experiment show that both GE and VT lessen the extent of myocardial ischemic lesions and exhibit cardioprotective activity.

White random-bred male rats weighing approximately 200 g were anesthetized using a light ether administration and then immobilized and artificially ventilated. The descending branch of the left coronary artery was ligated using the technique disclosed by Selye et al., *Angiology* 11: 398–407 (1960). Immediately after ligation, a test substance, positive, control substance, or negative control substance (described below) was administered to a rat through a catheterized femoral vein. Each dose of each test substance or positive or negative control substance was administered to an experimental or control group of 9 test rats. In this study, GE and VT served as test substances, propranolol served as the positive control substance, and physiological saline served as the negative control substance. Each test rat in an experimental group was given a dose of either 0.1, 1.0, or 10.0 milligram GE per kilogram of body weight of the subject animal (mg/kg) or 0.1, 1.0, or 10.0 milligram VT per kilogram of body weight of the animal. Each animal of the positive control group received an intravenous dose of 0.5 mg of β-adrenergic blocking agent, propranolol (Obzidan, Germed, Germany) per kilogram of body weight. Propranolol is commonly used to manage cardiac arrhythmia and there is some evidence that the agent may reduce the extent of ischemic damage to the heart. See GOODMAN AND GILMAN'S THE PHARMACOLOGICAL BASIS OF THERAPEUTICS, supra, at 192. Each animal of the negative control group received physiological saline.

One hour after initiation of the coronary artery occlusion, each test animal was sacrificed, its blood was collected, and the CPK activity in its blood serum was measured. CPK activity was determined by using a standard biochemical method, such as that commercially available from the Lachema Company (Czechia) in its test kit, and by following the manufacturer's process instructions included in the package insert.

As a supplementary control for the possible trauma caused by the surgical procedure, a group of 9 sham-operated rats was included in the study. These test animals were subjected to chest dissection, but not to coronary artery occlusion. These "sham-operated" animals were not treated with any test or control substances and were euthanized 1 hour after surgery. Their blood was then collected for determination of CPK activity.

The results of this study are presented in Table 13. Doses of GE at 0.1, 1.0, and 10.0 milligram were each found to diminish the extent of induced myocardial ischemic lesions in the test rats, as measured by a significant reduction in the CPK activity in the blood serum relative to the negative control (i.e., the release of the intracellular myocardial enzyme into serum was measured to monitor the extent of damage resulting following coronary artery ligation). VT produced similar results at doses of 0.1 and 1.0 mg/kg, respectively. Animals with induced myocardial ischemic lesions that were treated with GE or VT had CPK activities in serum that were not significantly different from those observed in the group of sham-operated animals.

The biological activities of GE and VT observed in this model are comparable with those activities previously disclosed for outward potassium flow activators tested in parallel animal models. Pharmaceutical compounds having potassium channel opener activities have been shown to exert cardioprotective effects on ischemic myocardium, to diminish enzyme "leakage," and to optimize the expenditure of macroergic phosphates. As demonstrated in this experiment, GE and VT appear to produce effects that are identical to or at least similar to known compounds having potassium channel opener activities.

TABLE 13

The Effects of GE and VT on CPK Activity in Blood Serum 1 Hour after Coronary Occlusion

| Substance | Dose (mg/kg) | CPK Activity (mcCat/L) |
|---|---|---|
| Sham-operated animals | — | 0.063 (±0.011) |
| S | — | 0.263 (±0.032)$^{\&}$ |
| Propranolol | — | 0.170 (±0.011)*$^{\&}$ |
| GE | 0.1 | 0.062 (±0.013)*$^{\#}$ |
| | 1.0 | 0.056 (±0.014)*$^{\#}$ |
| | 10.0 | 0.110 (±0.024)*$^{\#}$ |

TABLE 13-continued

The Effects of GE and VT on CPK Activity in Blood Serum 1 Hour after Coronary Occlusion

| Substance | Dose (mg/kg) | CPK Activity (mcCat/L) |
|---|---|---|
| VT | 0.1 | 0.119 (±0.032)* |
|  | 1.0 | 0.129 (±0.020)&* |
|  | 10.0 | 0.176 (±0.033)& |

Significantly different (P < 0.05, Student's t-test) from values recorded for following groups:
&sham-operated animals,
*negative control,
positive control.
Abbreviation: S = Physiological saline.

Example 6

Antiarrhythmic Effects of GE and VT on in a Model of Chloroform-Induced Arrhythmia Chloroform inhalation induces ventricular arrhythmia and is widely used as a screening test for inducing arrhythmia in animal models and identifying substances and compounds possessing antiarrhythmic activity. In mice, deep chloroform anesthesia gives rise to ventricular tachycardia and/or ventricular fibrillation. Although the mechanism of these arrhythmogenic effects has not been clearly elucidated, there is some evidence that the myocardial cells of mice that have been anesthetized with chloroform have a shortened refractory period and exhibit a desynchronization of their excitability recovery. Presumably, these conditions contribute to the occurrence of the re-entry type of arrhythmias. Moreover, chloroform heightens sensitivity of the myocardium to endogenous catecholamines thus increasing their arrhythmogenic effects. Winslow, Pharmac. Ther. 24: 401–433 (1984).

The results of this study demonstrate that GE and VT exhibit antiarrhythmic activities and cardioprotective effects in animal models in which ventricular arrhythmia has been induced. This study was conducted on the basis of recommendations of the General Pharmacology Service Program (Current Test Protocols PAN Laboratory).

Each mouse in the study was treated by intraperitoneal injection of a dose of a test or control substance 15 minutes prior to the administration of a deep chloroform anesthesia. A test or control substance was then administered to each mouse. GE and VT served as test substances, and each peptide was examined at doses of 0.001, 0.01, 0.1, 1.0, and 10.0 mg/kg. Novocainamide, a known antiarrhythmic agent, served as the positive control substance and was administered to mice in the positive control group at a dose of 240 mg/kg. Physiological saline served as the negative control substance and was administered to the mice in the negative control group.

Chloroform anesthesia was administered to each mouse by placing the mouse in an airtight glass container with cotton wool soaked in 20 ml of absolute chloroform. At the moment of respiratory arrest, the mouse was removed from the jar and electrocardiogram (ECG) monitoring (standard lead II) was initiated and continued for 30 seconds. According to General Pharmacology Service Program criteria, a substance has a protective antiarrhythmic effect if, following its administration to a test animal, the test animal shows no sign of ventricular paroxysmal rhythm disturbance (e.g., ventricular tachycardia or ventricular fibrillation) during the 30-second interval of respiratory arrest induced by the chloroform, and if the heart rate of the test animal during that 30-second period remains below 100 beats per 30 seconds. An antiarrhythmic activity for a particular dose of a test substance is pharmaceutically acceptable if 30% of the animals in a test group show the latter test results (i.e., namely, no sign of ventricular paroxysmal rhythm disturbances and heart rate below 100 beats per 30 seconds within 30 seconds following the respiratory arrest).

The results of this study are presented in Table 14. Pretreatment of mice with GE or VT at a dose of 0.01, 0.1, 1.0, or 10.0 mg/kg was found to prevent the development of ventricular arrhythmias induced by inhalation of toxic doses of chloroform or coronary occlusion. The protective antiarrhythmic effects exhibited by both GE and VT were not significantly different from the protective antiarrhythmic effects produced by novocainamide at a dose of 240.0 mg/kg.

TABLE 14

The Antiarrhythmic Effects of GE and VT in an Animal Model of Chloroform-Induced Arrhythmia

| Substance | Dose mg/kg | Antiarrhythmic Effect (no. animals) | | Result |
|---|---|---|---|---|
|  |  | abs | % |  |
| S | — | 0 | 0 | No effect |
| Novocainamide | 240 | 7 | 77.8* | Antiarrhythmic effect |
| GE | 0.001 | 1 | 11.1 | No effect |
|  | 0.01 | 4 | 44.4* | Antiarrhythmic effect |
|  | 0.1 | 4 | 44.4* | Antiarrhythmic effect |
|  | 1.0 | 5 | 55.6* | Antiarrhythmic effect |
|  | 10.0 | 6 | 66.7*# | Antiarrhythmic effect |
| VT | 0.001 | 0 | 0# | No effect |
|  | 0.01 | 3 | 33.3# | Antiarrhythmic effect |
|  | 0.1 | 4 | 44.6* | Antiarrhythmic effect |
|  | 1.0 | 6 | 66.7* | Antiarrhythmic effect |
|  | 10.0 | 4 | 44.4* | Antiarrhythmic effect |

*Significantly different (P < 0.05, Chi-squared test) from negative control group values.
Significantly different (P < 0.05, Chi-squared test) from positive control group values.
Abbreviation: S = Physiological saline.

Example 7

Effects of GE and VT on Occurrence, Frequency and Duration of Early Ischemic Arrhythmias Ischemic arrhythmias that occur during the first 20 to 30 minutes following coronary occlusion are among the most formidable complications of acute myocardial ischemia because they are often irreversible in character and can result in sudden death. The mechanisms by which these arrhythmias are generated appears to result from re-entrant myocardial excitation. In this experiment, it is demonstrated that both GE and VT reduce the duration of ventricular tachycardias in ischemic myocardium.

White random-bred male rats weighing 200 g were given light ether anesthesia and were then immobilized and artificially ventilated. The descending branch of the left coronary artery of each rat was ligated. Immediately following ligation, a test or control substance was administered to each rat through the catheterized femoral vein, and an ECG recording was initiated (standard lead II) and maintained for the next 30 minutes.

GE and VT served as test substances and were administered to animals in the respective test groups at doses of 0.1, 1.0, and 10.0 mg/kg. The β-adrenergic blocking agent, propranolol (Obzidan, Germed, Germany), served as the positive control substance and was administered intravenously to each animal in the positive control group at a dose of 0.5 mg/kg. Physiological saline served as the negative control substance and was administered intravenously to animals in the negative control group. Each dose of each test or control substance was tested separately on a group of nine animals.

The following parameters were evaluated based upon the ECG recordings: (i) the number of ventricular extrasystoles that occurred within a 30-minute observation period following coronary occlusion; (ii) the overall cumulative duration of ventricular tachycardias (i.e., the summation of duration of individual paroxysmal ventricular rhythm disturbances in seconds) occurring within the 30-minute observation period; and (iii) the overall duration (in seconds) of the ventricular fibrillations occurring within the 30-minute observation period. The data were processed electronically and statistical comparisons were made between the values obtained from the animals in the experimental test groups and those in the different respective control groups.

The results of this experiment are presented in Table 15. No ventricular fibrillations were recorded in this study. As is indicated in Table 15, all of the tested doses of GE and VT in this model reduced the overall duration of ventricular tachycardias in ischemic myocardium. Doses of GE of 0.1 mg/kg and 10.0 mg/kg and a dose of VT of 10.0 mg/kg were particularly effective in reducing the overall duration of these ventricular tachycardias. Doses of GE at 0.1 mg/kg and 10.0 mg/kg and doses of VT at 1.0 and 10.0 mg/kg were found to decrease the overall duration of ventricular tachycardia. Notably, a dose of VT at 10 mg/kg induced a 3-fold decrease in the number of ventricular extrasystoles as compared with the negative control group.

TABLE 15

The Antiarrhythmic Effects of GE and VT on Early Ischemic Myocardial Arrhythmias

| Substance | Dose (mg/kg) | Overall Duration of Ventricular Tachycardia (sec) | Number of Ventricular Extrasystoles |
| --- | --- | --- | --- |
| S | — | 159.91 (±24.24) | 65.33 (±18.19) |
| Obzidan | 0.5 | 56.74 (±17.24)* | 61.22 (±27.02) |
| GE | 0.1 | 38.67 (±12.19)* | 25.22 (±8.36) |
|  | 1.0 | 93.17 (±25.90) | 116.22 (±22.06) |
|  | 10.0 | 51.78 (±20.98)* | 47.78 (±17.96) |
| VT | 0.1 | 105.60 (±33.89) | 131.78 (±38.48) |
|  | 1.0 | 88.56 (±17.07)* | 51.33 (±10.12) |
|  | 10.0 | 46.58 (±15.85)* | 18.00 (±8.43)* |

*Significantly different ($P < 0.05$, Student's t-test) from negative control group values.
Abbreviation: S = Physiological saline.

Example 8

Effects of GE and VT on Arterial Blood Pressure

In this experiment, the effects of GE and VT on arterial blood pressure were examined. The results of this experiment demonstrate that both GE and VT reduce arterial blood pressure and exhibit hypotensive (i.e., cause reduction in blood pressure) and vasodilating effects in subjects to which these dipeptides have been administered. These effects are characteristic features of known potassium channel openers.

White random-bred male rats weighing approximately 200 g were employed for this study. Each dose of each respective test or control substance was administered to a group of five rats. GE and VT were employed as test substances and were administered intravenously at doses of 0.01, 0.1, 1.0, and 10.0 mg/kg. Physiological saline (0.2 ml) served as the negative control substance. The ganglionic blocking agent, pentamine, served as the positive control substance and was tested at a dose of 5 mg/kg. Following administration of the test substance, positive control substance, or negative control substance, the arterial blood pressure of each animal was monitored.

Prior to administration of the test or control substance, each animal was anesthetized with Chloralose and then both its carotid artery and jugular vein were catheterized. The carotid catheter was connected to an electronic manometer attached to a computer recorder through an analog-to-digital converter. The mean basal level of the arterial blood pressure was determined as follows: For a period of 30 seconds, the digital signal pertaining to the arterial blood pressure was recorded at 1-second intervals. The mean value of these thirty individual measurements was then determined and recorded.

After determining the mean basal level of the arterial blood pressure, a particular dose of the test or control substance was administered in a volume of 0.2 ml of physiological saline to an animal through the jugular venous catheter. Measurements of the arterial blood pressure were then taken during the next 1.5 hours as follows: (i) during the first 5 minutes, the arterial blood pressure was being monitored continuously and mean values were calculated electronically and recorded at each of the ten different 30-second intervals (i.e., $30^{th}$ second, $60^{th}$ second, etc.); (ii) thereafter, mean values of the arterial blood pressure were calculated at the first seconds of 10th minute, 15th minute, 30th minute, 45th minute, 60th minute, 75th minute, and 90th minute after administration of the respective test or control substance.

The results of this study are shown in Tables 16A and 16B. In this model, the arterial blood pressure of animals treated with physiological saline (negative control substance) remained at about 92 to about 100% of pretreatment basal levels during the 90-minute observation period. Pentamine was found to reduce arterial blood pressure to about 68 to about 75% of pretreatment basal levels during the first 5 minutes following its administration, confirming that this animal model responds to vasodilating agents. Treatment with either GE or VT was found to cause a moderate, but delayed, decrease in the mean arterial blood pressure after about 60 to 90 minutes. These results suggest that GE and VT each possess moderate vasodilating characteristics.

TABLE 16A

The Effect of GE on Arterial Blood Pressure

| Substance | Dose mg/kg | n | Basal Level | Time From Substance Administration (min) | | | | | |
|---|---|---|---|---|---|---|---|---|---|
| | | | | 1 | 2 | 3 | 4 | 5 | 10 |
| S | — | 5 | 100.00 | 99.76 (±1.16) | 101.16 (±1.24) | 98.38 (±1.67) | 97.96 (±1.85) | 99.85 (±1.99) | 94.53 (±1.56)* |
| Pentamine | 5 | 5 | 100.00 | 87.09 (±3.41)*@ | 68.18 (±8.81)*@ | 70.82 (±10.22)*@ | 69.29 (±8.68)*@ | 74.11 (±7.02)*@ | 91.63 (±5.91) |
| GE | 0.01 | 5 | 100.00 | 101.02 (±3.05)# | 102.72 (±2.35)# | 103.88 (±1.52)# | 99.77 (±3.27)# | 102.90 (±1.38)# | 96.17 (±4.00) |
| | 0.1 | 5 | 100.00 | 96.00 (±3.92) | 96.60 (±4.13)# | 97.66 (±3.17)# | 97.32 (±2.48)# | 98.31 (±1.44)# | 96.04 (±2.59) |
| | 1.0 | 5 | 100.00 | 70.32 (±8.40) | 84.63 (±7.88) | 90.73 (±5.45) | 93.72 (±2.43)# | 98.11 (±0.92)# | 94.67 (±1.92)# |
| | 10.0 | 5 | 100.00 | 94.68 (±2.77) | 100.17 (±3.38)# | 101.63 (±3.02)# | 101.22 (±2.46)# | 100.20 (±0.82)# | 95.61 (±2.95) |

| Substance | Dose mg/kg | n | Basal Level | Time From Substance Administration (min) | | | | | |
|---|---|---|---|---|---|---|---|---|---|
| | | | | 15 | 30 | 45 | 60 | 75 | 90 |
| S | — | 5 | 100.00 | 92.50 (±1.56)* | 96.58 (±4.14) | 94.50 (±2.91) | 96.70 (±4.48) | 95.52 (±4.21) | 96.81 (±4.91) |
| Pentamine | 5 | 5 | 100.00 | 89.94 (±5.46) | 86.95 (±4.01)* | 93.89 (±1.92)* | 100.31 (±1.24) | 94.38 (±1.05)* | 93.22 (±3.56) |
| GE | 0.01 | 5 | 100.00 | 97.01 (±5.71) | 98.26 (±1.02)# | 99.01 (±2.44) | 93.29 (±8.47) | 94.15 (±5.23) | 102.09 (±2.91) |
| | 0.1 | 5 | 100.00 | 94.98 (±2.20) | 93.56 (±4.634) | 80.15 (±12.67) | 83.03 (±10.28) | 83.37 (±10.40) | 84.50 (±10.48) |
| | 1.0 | 5 | 100.00 | 92.70 (±2.49) | 90.58 (±4.46) | 88.43 (±6.09) | 88.85 (±6.49) | 90.07 (±5.71) | 89.82 (±5.10) |
| | 10.0 | 5 | 100.00 | 91.27 (±6.20) | 88.24 (±7.88)# | 89.56 (±6.42) | 85.99 (±7.76) | 87.12 (±6.35) | 78.69 (±9.76) |

*Significantly different (paired Student's t-test) from basal level. Significantly different (unpaired Student's t-test) vs. parameter values in groups of: @—negative control group (saline injection), and #—positive control group (pentamine injection) at a corresponding minute.
Abbreviation: S = Physiological saline.

TABLE 16B

The Effect of VT on Arterial Blood Pressure

| Substance | Dose mg/kg | n | Basal Level | Time From Substance Administration (min) | | | | | |
|---|---|---|---|---|---|---|---|---|---|
| | | | | 1 | 2 | 3 | 4 | 5 | 10 |
| S | — | 5 | 100.00 | 99.76 (±1.16) | 101.16 (±1.24) | 98.38 (±1.67) | 97.96 (±1.85) | 99.85 (±1.99) | 94.53 (±1.56)* |
| Pentamine | 5 | 5 | 100.00 | 87.09 (±3.41)*@ | 68.18 (±8.81)*@ | 70.82 (±10.22)*@ | 69.29 (±8.68)*@ | 74.11 (±7.02)*@ | 91.63 (±5.91) |
| VT | 0.01 | 5 | 100.00 | 100.43 (±0.61)# | 102.91 (±1.55)# | 102.64 (±1.48)# | 102.82 (±1.60)# | 102.20 (±1.74)# | 104.19 (±2.34)@ |
| | 0.1 | 5 | 100.00 | 96.32 (±3.00) | 95.49 (±2.90)# | 96.75 (±3.52)# | 97.02 (±3.32)# | 96.12 (±3.42)# | 88.85 (±9.02) |
| | 1.0 | 5 | 100.00 | 93.39 (±6.55) | 91.46 (±10.15) | 96.91 (±3.40)# | 97.40 (±2.55)# | 96.72 (±2.41)# | 97.05 (±0.69)* |
| | 10.0 | 5 | 100.00 | 78.46 (±9.34) | 80.96 (±10.43) | 81.99 (±9.80) | 87.13 (±8.04) | 92.77 (±5.16) | 93.85 (±2.66) |

| Substance | Dose mg/kg | n | Basal Level | Time From Substance Administration (min) | | | | | |
|---|---|---|---|---|---|---|---|---|---|
| | | | | 15 | 30 | 45 | 60 | 75 | 90 |
| S | — | 5 | 100.00 | 92.50 (±1.56)* | 96.58 (±4.14) | 94.50 (±2.91) | 96.70 (±4.48) | 95.52 (±4.21) | 96.81 (±4.91) |
| Pentamine | 5 | 5 | 100.00 | 89.94 (±5.46) | 86.95 (±4.01)* | 93.89 (±1.92)* | 100.31 (±1.24) | 94.38 (±1.05)* | 93.22 (±3.56) |
| VT | 0.01 | 5 | 100.00 | 100.43 (±0.61)# | 102.91 (±1.55)# | 102.64 (±1.48)# | 102.82 (±1.60)# | 102.20 (±1.74)# | 104.19 (±2.34)@ |
| | 0.1 | 5 | 100.00 | 96.32 (±3.00) | 95.49 (±2.90)# | 96.75 (±3.52)# | 97.02 (±3.32)# | 96.12 (±3.42)# | 88.85 (±9.02) |
| | 1.0 | 5 | 100.00 | 93.39 (±6.55) | 91.46 (±10.15) | 96.91 (±3.40)# | 97.40 (±2.55)# | 96.72 (±2.41)# | 97.05 (±0.69)* |

TABLE 16B-continued

The Effect of VT on Arterial Blood Pressure

| 10.0 | 5 | 100.00 | 78.46 (±9.34) | 80.96 (±10.43) | 81.99 (±9.80) | 87.13 (±8.04) | 92.77 (±5.16) | 93.85 (±3.66) |
|---|---|---|---|---|---|---|---|---|

*Significantly different (paired Student's t-test) from basal level. Significantly different (unpaired Student's t-test) vs. parameter values in groups of: @—negative control group (saline injection), and #—positve control group (pentamine injection) at a corresponding minute.
Abbreviation: S = Physiological saline.

Example 9

Effects of GE and VT on Cardiac Function

This experiment was designed to investigate the effects of GE and VT on cardiac function. The results of this investigation reveal that neither GE nor VT has a significant effect on the functioning of a normal heart. Notably, neither of these dipeptides alters the basic characteristics of a normal electrocardiogram (ECG).

White random-bred male rats weighing about 200 g were anesthetized using Nembutal. A basal ECG was taken as soon as possible following anesthetization to establish basal measurements for the principal parameters of cardiac functions. Rats showing any deviation from normal ECG parameters were excluded from the study.

GE and VT served as the test substances. To each animal in the test group, either GE or VT at a dose of 0.001, 0.01, 0.1, 1.0, 10.0, and 100.0 mg/kg was administered intravenously. Each dose of each test substance was evaluated on a separate experimental group consisting of 10 rats. ECG traces (no less than 4 complexes each) were taken at 1, 3, 5, and 10 minutes after the injection of the test substance. Physiological saline served as the negative control substance. To each animal in the negative control group, 2 ml of physiological saline was injected intravenously.

Cardiac function was evaluated by monitoring the following ECG parameters:

(i) the duration of the PQ interval (which defines the time the impulse passes over the atria and the atrioventricular node). The normal value for this parameter for Nembutal-anesthetized rats is 25 to 60 milliseconds (ms) using a lead II ECG.

(ii) the width of the QRS complex (which defines the impulse passage over the ventricular myocardium). The normal value for this parameter for Nembutal- anesthetized rats is 15 to 30 msec using a lead II ECG.

(iii) the voltage of the R-wave (which defines the spread of excitation over the left ventricle). The normal value for this parameter for Nembutal-anesthetized rats is 0.163 to 0.9 millivolts (mV) using lead II ECG.

(iv) the duration of the QT interval (which defines the time from the beginning of the QRS complex to the end of the T wave and reflects the duration of ventricular depolarization and repolarization). The normal value for this parameter for Nembutal-anesthetized rats is 50 to 106 ms using lead II ECG.

(v) the voltage of the T-wave (which defines the repolarization process in the left ventricle). The normal value for this parameter for Nembutal-anesthetized rats is 0.05 to 0.38 mV using lead II ECG.

As shown in Tables 17A through 21B, for the dose ranges tested, GE and VT had no significant effect on any of these standard parameters of heart function. Even in those few instances where, for a given parameter, a statistically significant difference was observed between the initial value and a later-measured value(s), the later-measured values were within the normal range.

TABLE 17A

The Effect of GE on Duration of PQ Interval (% Initial Mean Value)

| Substance | Dose mg/kg | Time From Substance Administration (min) | | | |
|---|---|---|---|---|---|
| | | 1 | 3 | 5 | 10 |
| S | — | 93.75 (±5.35) | 110.59 (±8.39) | 108.31 (±7.35) | 108.51 (±8.39) |
| GE | 0.001 | 99.74 (±4.78) | 98.42 (±4.28) | 103.01 (±5.89) | 104.96 (±7.36) |
| | 0.01 | 115.72 (±6.34)*# | 105.79 (±4.13) | 109.65 (±3.60)* | 103.17 (±4.52) |
| | 1.0 | 107.30 (±5.94) | 95.03 (±3.56) | 99.18 (±6.67) | 102.38 (±4.40) |
| | 10.0 | 100.38 (±4.93) | 99.92 (±4.08) | 98.87 (±4.87) | 94.70 (±4.99) |
| | 100.0 | 103.51 (±3.40) | 99.07 (±2.99) | 102.80 (±3.99) | 99.97 (±4.17) |

Significantly different ($P < 0.05$, paired Student's t-test) vs.:
*- corresponding initial level;
- parameter values in the control group at a corresponding minute.
Abbreviation: S = Physiological saline.

TABLE 17B

The Effect of VT on Duration of PQ Interval (% Initial Mean Value)

| Substance | Dose mg/kg | Time From Substance Administration (min) | | | |
|---|---|---|---|---|---|
| | | 1 | 3 | 5 | 10 |
| S | — | 93.75 (±5.35) | 110.59 (±8.39) | 108.31 (±7.35) | 108.51 (±8.39) |
| VT | 0.001 | 107.20 (±4.61) | 108.87 (±6.72) | 107.04 (±6.05) | 108.39 (±5.26) |
| | 0.01 | 101.70 (±3.63) | 102.23 (±6.42) | 101.58 (±5.34) | 103.58 (±7.02) |
| | 0.1 | 96.37 (±2.88) | 99.99 (±4.66) | 101.55 (±2.54) | 100.12 (±1.90) |
| | 1.0 | 102.33 (±2.73) | 103.40 (±2.57) | 103.31 (±2.82) | 99.43 (±3.95) |
| | 10.0 | 106.10 (±4.41) | 109.78 (±7.96) | 108.95 (±4.60) | 107.05 (±5.51) |
| | 100.0 | 100.00 (±0.00) | 102.86 (±2.86) | 100.00 (±0.00) | 100.00 (±0.00) |

Abbreviation: S = Physiological saline.

TABLE 18A

The Effect of GE on Width of QRS Complex (% Initial Mean Value)

| Substance | Dose mg/kg | Time From Substance Administration (min) | | | |
|---|---|---|---|---|---|
| | | 1 | 3 | 5 | 10 |
| S | — | 100.00 (±0.00) | 100.00 (±0.00) | 110.00 (±0.00) | 110.00 (±0.00) |

TABLE 18A-continued

The Effect of GE on Width of QRS Complex (% Initial Mean Value)

| Substance | Dose mg/kg | 1 | 3 | 5 | 10 |
|---|---|---|---|---|---|
| GE | 0.001 | 100.00 (±0.00) | 100.00 (±0.00) | 100.00 (±0.00) | 100.00 (±0.00) |
|  | 0.01 | 100.00 (±0.00) | 100.00 (±0.00) | 100.00 (±0.00) | 100.00 (±0.00) |
|  | 0.1 | 102.00 (±2.00) | 102.00 (±2.00) | 102.00 (±2.00) | 100.33 (±2.47) |
|  | 1.0 | 99.29 (±5.83) | 109.32 (±6.01) | 113.78 (±10.53) | 101.14 (±11.05) |
|  | 10.0 | 104.40 (±5.67) | 98.58 (±3.97) | 97.57 (±5.89) | 102.15 (±5.99) |
|  | 100.0 | 101.67 (±1.67) | 100.00 (±0.00) | 100.00 (±0.00) | 100.00 (±0.00) |

Abbreviation: S = Physiological saline.

TABLE 18B

The Effect of VT on Width of QRS Complex (% Initial Mean Value)

| Substance | Dose mg/kg | 1 | 3 | 5 | 10 |
|---|---|---|---|---|---|
| S | — | 100.00 (±0.00) | 100.00 (±0.00) | 110.00 (±0.00) | 110.00 (±0.00) |
| VT | 0.001 | 102.50 (±7.66) | 100.00 (±6.45) | 105.67 (±11.68) | 105.00 (±0.00) |
|  | 0.01 | 100.00 (±0.00) | 100.00 (±0.00) | 100.00 (±0.00) | 100.00 (±0.00) |
|  | 0.1 | 102.00 (±2.00) | 102.00 (±2.00) | 102.00 (±2.00) | 100.33 (±2.47) |
|  | 1.0 | 99.29 (±5.83) | 100.32 (±6.01) | 113.78 (±10.53) | 101.14 (±11.05) |
|  | 10.0 | 104.40 (±5.67) | 98.58 (±3.97) | 97.57 (±5.89) | 102.15 (±5.99) |
|  | 100.0 | 101.67 (±1.67) | 100.00 (±0.00) | 100.00 (±0.00) | 100.00 (±0.00) |

Abbreviation: S = Physiological saline.

TABLE 19A

The Effect of GE on the R-Wave Voltage (% of Initial Mean Value)

| Substance | Dose mg/kg | 1 | 3 | 5 | 10 |
|---|---|---|---|---|---|
| S | — | 102.88 (±2.60) | 102.20 (±4.89) | 103.36 (±4.29) | 106.21 (±8.22) |
| GE | 0.001 | 98.63 (±1.55) | 98.88 (±1.60) | 97.86 (±1.20) | 98.63 (±1.55) |
|  | 0.01 | 102.20 (±3.38) | 104.62 (±2.81) | 102.15 (±3.66) | 102.17 (±4.10) |
|  | 0.1 | 103.63 (±4.41) | 102.80 (±5.21) | 102.74 (±5.26) | 103.81 (±5.67) |
|  | 1.0 | 101.87 (±1.86) | 102.38 (±2.91) | 104.35 (±2.68) | 107.60 (±2.80)* |
|  | 10.0 | 102.97 (±2.58) | 105.82 (±4.11) | 103.51 (±3.60) | 104.78 (±3.60) |
|  | 100.0 | 96.62 (±2.33) | 100.45 (±3.67) | 99.74 (±3.30) | 102.25 (±2.76) |

*Significantly different (P < 0.05, paired Student's t-test) from corresponding initial level.
Abbreviation: S = Physiological saline.

TABLE 19B

The Effect of VT on the R-Wave Voltage (% of Initial Mean Value)

| Substance | Dose mg/kg | 1 | 3 | 5 | 10 |
|---|---|---|---|---|---|
| S | — | 102.88 (±2.60) | 102.20 (±4.89) | 103.36 (±4.29) | 106.21 (±8.22) |
| VT | 0.001 | 106.03 (±4.20) | 100.74 (±4.00) | 104.34 (±3.22) | 101.32 (±3.36) |
|  | 0.01 | 107.95 (±4.21) | 107.66 (±5.94) | 106.79 (±5.60) | 110.95 (±8.12) |
|  | 0.1 | 105.29 (±2.40) | 105.82 (±2.77) | 102.17 (±2.17) | 103.73 (±2.30) |
|  | 1.0 | 96.68 (±2.27) | 95.28 (±1.44)* | 94.74 (±2.25)* | 93.52 (±3.07) |
|  | 10.0 | 99.80 (±2.05) | 97.46 (±1.29) | 98.49 (±2.16) | 98.69 (±2.68) |
|  | 100.0 | 102.04 (±2.04) | 102.04 (±2.04) | 103.34 (±2.23) | 102.24 (±2.72) |

*Significantly different (P < 0.05, paired Student's t-test) from corresponding initial level.
Abbreviation: S = Physiological saline.

TABLE 20A

The Effect of GE on Duration of QT Interval (% of Initial Mean Value)

| Substance | Dose mg/kg | 1 | 3 | 5 | 10 |
|---|---|---|---|---|---|
| S | — | 105.60 (±3.39) | 101.43 (±5.74) | 102.92 (±5.16) | 98.15 (±3.88) |
| GE | 0.001 | 102.50 (±6.34) | 94.33 (±7.50) | 97.83 (±6.56) | 89.61 (±8.53) |
|  | 0.01 | 105.68 (±3.39) | 102.58 (±4.26) | 106.74 (±4.94) | 102.86 (±3.84) |
|  | 0.1 | 97.76 (±3.45) | 96.73 (±5.14) | 95.17 (±5.42) | 91.84 (±5.40) |
|  | 1.0 | 101.77 (±4.89) | 99.08 (±3.65) | 100.34 (±5.74) | 93.90 (±4.80) |
|  | 10.0 | 94.63 (±2.83)# | 102.86 (±3.20) | 103.00 (±3.19) | 101.74 (±3.86) |
|  | 100.0 | 100.60 (±3.65) | 100.67 (±2.83) | 97.82 (±3.73) | 94.295 (±3.07) |

Significantly different (P < 0.05, paired Student's t-test) from parameter values in the control group at a corresponding minute.
Abbreviation: S = Physiological saline.

TABLE 20B

The Effect of VT on Duration of QT Interval (% of Initial Mean Value)

| Substance | Dose mg/kg | 1 | 3 | 5 | 10 |
|---|---|---|---|---|---|
| S | — | 105.60 (±3.39) | 101.43 (±5.74) | 102.92 (±5.16) | 98.15 (±3.88) |
| VT | 0.001 | 101.80 (±5.54) | 105.73 (±5.46) | 102.20 (±6.81) | 101.24 (±5.79) |
|  | 0.01 | 99.86 (±3.54) | 101.48 (±3.63) | 101.09 (±3.26) | 97.32 (±3.39) |
|  | 0.1 | 102.97 (±3.17) | 98.39 (±3.17) | 95.65 (±3.21) | 90.67 (±3.54) |
|  | 1.0 | 105.57 (±6.58) | 105.58 (±6.61) | 102.18 (±7.96) | 101.18 (±7.58) |
|  | 10.0 | 94.89 (±3.26)# | 95.91 (±3.60) | 96.52 (±3.78) | 88.88 (±3.42)* |
|  | 100.0 | 100.00 (±0.00) | 100.82 (±3.78) | 97.96 (±2.04) | 94.74 (±2.52) |
|  | 10.0 | 102.97 (±2.58) | 105.82 (±4.11) | 103.51 (±3.60) | 104.78 (±3.60) |

TABLE 20B-continued

The Effect of VT on Duration of QT Interval (% of Initial Mean Value)

| Substance | Dose mg/kg | \_\_\_\_Time From Substance Administration (min)\_\_\_\_ | | | |
|---|---|---|---|---|---|
| | | 1 | 3 | 5 | 10 |
| | 100.0 | 96.62 (±2.33) | 100.45 (±3.67) | 99.74 (±3.30) | 102.25 (±2.76) |

Significantly different (P < 0.05, paired Student's t-test) vs.:
*- corresponding initial level;
- parameter values in the control group at corresponding minute.
Abbreviation: S = Physiological saline.

TABLE 21A

The Effect of GE on T-Wave Voltage (% of Initial Mean Value)

| Substance | Dose mg/kg | \_\_\_\_Time From Substance Administration (min)\_\_\_\_ | | | |
|---|---|---|---|---|---|
| | | 1 | 3 | 5 | 10 |
| S | — | 99.31 (±4.44) | 107.13 (±5.66) | 105.85 (±4.20) | 112.54 (±7.46) |
| GE | 0.001 | 99.17 (±9.82) | 105.50 (±9.53) | 110.00 (±9.69) | 100.72 (±13.51) |
| | 0.01 | 97.81 (±4.62) | 104.28 (±3.52) | 101.69 (±6.49) | 105.67 (±6.83) |
| | 0.1 | 97.90 (±3.34) | 99.92 (±3.62) | 103.63 (±4.62) | 103.25 (±7.75) |
| | 1.0 | 98.54 (±3.47) | 96.11 (±4.73) | 99.82 (±3.92) | 99.71 (±4.52) |
| | 10.0 | 97.27 (±3.62) | 104.28 (±6.29) | 96.80 (±5.44) | 94.67 (±4.52) |
| | 100.0 | 108.35 (±3.52)* | 109.59 (±5.92) | 96.71 (±3.12) | 108.93 (±5.45) |

*Significantly different (P < 0.05, paired Student's t-test) from corresponding initial level.
Abbreviation: S = Physiological saline.

TABLE 21B

The Effect of VT on T-Wave Voltage (% of Initial Mean Value)

| Substance | Dose mg/kg | \_\_\_\_Time From Substance Administration (min)\_\_\_\_ | | | |
|---|---|---|---|---|---|
| | | 1 | 3 | 5 | 10 |
| S | — | 99.31 (±4.44) | 107.13 (±5.66) | 105.85 (±4.20) | 112.54 (±7.45) |
| VT | 0.001 | 105.36 (±4.95) | 111.12 (±6.12) | 107.40 (±8.16) | 109.87 (±6.97) |
| | 0.01 | 103.91 (±3.91) | 102.55 (±5.72) | 109.96 (±3.37)* | 102.30 (±4.59) |
| | 0.1 | 100.21 (±5.44) | 101.07 (±6.38) | 105.61 (±4.02) | 105.40 (±4.61) |
| | 1.0 | 112.11 (±6.54) | 110.44 (±6.23) | 102.45 (±8.54) | 101.73 (±8.64) |
| | 10.0 | 97.47 (±4.01) | 95.94 (±2.24) | 99.08 (±4.71) | 93.04 (±4.22)# |
| | 100.0 | 102.20 (±2.20) | 101.72 (±7.28) | 101.72 (±7.28) | 101.72 (±7.28) |

Significantly different (P < 0.05, paired Student's t-test) vs.:
*- corresponding initial level;
- parameter values in the control group at a corresponding minute.
Abbreviation: S = Physiological saline.

While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the and are encompassed by the claims of the invention. The scope of the invention should, therefore, be determined not with reference to the above description, but instead should be determined with reference to the appended claims along with their full scope of equivalents. All publications and patent documents cited in this application are incorporated by reference in their entirety for all purposes to the same extent as if each individual publication or patent document were so individually denoted.

What is claimed is:

1. A peptide polymer comprising at least two dipeptides, wherein each said dipeptide of said polymer is L-Gly-L-Glu or L-Val-L-Thr.

2. A pharmaceutical composition in unit dosage form comprising per unit dosage a range of from about 0.01 mg to about 1000 mg of L-Gly-L-Glu or L-Val-L-Thr or a pharmaceutically acceptable salt thereof, and a pharmaceutically acceptable carrier.

3. The pharmaceutical composition as in claim 2, wherein the range is from about 1 mg to about 100 mg.

4. The pharmaceutical composition of claim 2, wherein the composition comprises per unit dosage a range of from about 0.01 mg to about 1000 mg of L-Gly-L-Glu or a pharmaceutically acceptable salt thereof, and a pharmaceutically acceptable carrier.

5. The pharmaceutical composition of claim 2, wherein the composition comprises per unit dosage a range of from about 0.01 mg to about 1000 mg of L-Val-L-Thr or a pharmaceutically acceptable salt thereof, and a pharmaceutically acceptable carrier.

6. A kit useful for preserving a living tissue or a living organ, said kit comprising a container for holding the tissue or organ and an effective amount of a peptide for preserving the tissue or organ, wherein said peptide is L-Gly-L-Glu, L-Val-L-Thr, a polymer of two to eight dipeptides of L-Gly-L-Glu or L-Val-L-Thr, or a pharmaceutically acceptable salt thereof.

7. The kit of claim 6, wherein the effective amount of the peptide is within a range of from about $10^{-9}$M to about $10^{-5}$M.

8. A method for the prophylactic or therapeutic treatment of a disease responsive to opening of potassium channels in a subject in need thereof comprising administering to the subject an effective amount of a peptide, wherein said peptide is L-Gly-L-Glu, L-Val-L-Thr, a polymer of two to eight dipeptides, wherein each said dipeptide is L-Gly-L-Glu or L-Val-L-Thr, or a pharmaceutically acceptable salt thereof.

9. The method of claim 8, wherein the peptide is L-Gly-L-Glu or L-Val-L-Thr or a pharmaceutically acceptable salt thereof.

10. The method of claim 9, wherein the subject is a human.

11. The method of claim 10, wherein the effective amount of the peptide is within a range of from about 0.15 mg/kg to about 10 mg/kg.

12. The method of claim 10, wherein the disease involves bronchospastic conditions or bronchodilation.

13. The method of claim 10, wherein the disease is asthma.

14. The method of claim 10, wherein the disease is associated with hypoxia.

15. The method of claim 10, wherein the disease is associated with anoxia.

16. The method of claim 10, wherein the disease is epilepsy.

17. The method of claim 10, wherein the disease is cerebral ischemia.

18. The method of claim 10, wherein the disease is neurodegenerative disease.

19. The method of claim 10, wherein the disease is diabetes.

20. The method of claim 10, wherein the disease is Parkinson's disease.

21. The method of claim 10, wherein the disease is Alzheimer's disease.

22. The method of claim 10, wherein the disease is cirrhosis of the liver.

23. A method for the prophylactic or therapeutic treatment of a cardiovascular disease in a subject in need thereof comprising administering to the subject an effective amount of a peptide, wherein said peptide is L-Gly-L-Glu, L-Val-L-Thr, a polymer of two to eight dipeptides, wherein each said dipeptide is L-Gly-L-Glu or L-Val-L-Thr, or a pharmaceutically acceptable salt thereof.

24. The method of claim 23, wherein the peptide is L-Gly-L-Glu or L-Val-L-Thr or a pharmaceutically acceptable salt thereof.

25. The method of claim 24, wherein the subject is a human.

26. The method of claim 25, wherein the effective amount of the peptide is within a range of from about 0.15 mg/kg to about 10 mg/kg.

27. The method of claim 25, wherein the peptide is administered topically, systemically, intravenously, intraperitoneally, intramuscularly, subcutaneously, intranasally, transdermally, orally, or by intradermal injection, intrabronchial instillation, gastrointestinal delivery, or transmucosal delivery.

28. The method of claim 25, wherein the disease is ischemic heart disease.

29. The method of claim 25, wherein the disease is cardiac arrhythmia.

30. The method of claim 25, wherein the disease is hypertensive disease.

31. The method of claim 25, wherein the disease is congestive heart failure.

32. The method of claim 25, wherein the disease is responsive to vasodilation.

33. A method of inducing relaxation of a smooth muscle in a subject in need thereof comprising administering to the subject an effective amount of a peptide, wherein said peptide is L-Gly-L-Glu, L-Val-L-Thr, a polymer of two to eight dipeptides, wherein each said dipeptide is L-Gly-L-Glu or L-Val-L-Thr, or a pharmaceutically acceptable salt thereof.

34. The method of claim 33, wherein the peptide is L-Gly-L-Glu or L-Val-L-Thr or a pharmaceutically acceptable salt thereof.

35. The method of claim 34, wherein the subject is a human.

36. The method of claim 35, wherein the effective amount of the peptide is within a range of from about 0.15 mg/kg to about 10 mg/kg.

37. The method of claim 35, wherein the peptide is administered topically, systemically, intravenously, intraperitoneally, intramuscularly, subcutaneously, intranasally, transdermally, orally, or by intradermal injection, intrabronchial instillation, gastrointestinal delivery, or transmucosal delivery.

38. The method of claim 35, wherein the smooth muscle is intestinal smooth muscle.

39. The method of claim 35, wherein the smooth muscle is bronchial smooth muscle.

40. The method of claim 35, wherein the smooth muscle is tracheal smooth muscle.

41. The method of claim 35, wherein the smooth muscle is uterine smooth muscle.

42. The method of claim 35, wherein the smooth muscle is bladder smooth muscle.

43. The method of claim 35, wherein the smooth muscle is bowel smooth muscle.

44. The method of claim 35, wherein the smooth muscle is vascular smooth muscle.

45. The method of claim 44, wherein the relaxation of vascular smooth muscle produces vasodilation.

46. A method of inducing relaxation of a skeletal muscle in a subject in need thereof comprising administering to the subject an effective amount of a peptide, wherein said peptide is L-Gly-L-Glu, L-Val-L-Thr, a polymer of two to eight dipeptides, wherein each said dipeptide is L-Gly-L-Glu or L-Val-L-Thr, or a pharmaceutically acceptable salt thereof.

47. The method of claim 46, wherein the peptide is L-Gly-L-Glu or L-Val-L-Thr or a pharmaceutically acceptable salt thereof.

48. The method of claim 47, wherein the subject is a human.

49. The method of claim 48, wherein the effective amount of the peptide is within a range of from about 0.15 mg/kg to about 10 mg/kg.

50. The method of claim 48, wherein the peptide is administered topically, systemically, intravenously, intraperitoneally, intramuscularly, subcutaneously, intranasally, transdermally, orally, or by intradermal injection, intrabronchial instillation, gastrointestinal delivery, or transmucosal delivery.

51. A method for the prophylactic or therapeutic treatment of a disease responsive to opening of potassium channels in a subject in need thereof comprising administering to the subject an effective amount of a peptide having a potassium channel opener activity, wherein the peptide comprises a serial array of no more than about 16 L-amino acid residues, is extractable from myocardium in an acidic extract and isolatable therefrom in an included-volume of a G-25 superfine chromatographic resin, and has no effect on a tonic contraction of a smooth muscle specimen induced by a high potassium concentration.

52. A method of preserving a living tissue or a living organ comprising contacting the tissue or organ with a composition comprising a pharmaceutically acceptable carrier and an effective amount of a peptide, wherein said peptide is L-Gly-L-Glu or L-Val-L-Thr, a polymer of two to eight dipeptides of L-Gly-L-Glu or L-Val-L-Thr, or a pharmaceutically acceptable salt thereof.

53. The method of claim 52, wherein the effective amount of the peptide is within a range of from about $10^{-9}$M to about $10^{-5}$M.

54. The method of claim 8, further comprising administering to the subject an increasing amount of the peptide over time until the effective amount of said peptide is achieved at a tissue site to be treated or in blood of the subject.

55. The method of claim 8, wherein the peptide is L-Gly-L-Glu or a pharmaceutically acceptable salt thereof.

56. The method of claim 8, wherein the peptide is L-Val-L-Thr or a pharmaceutically acceptable salt thereof.

57. The method of claim 23, wherein the peptide is L-Gly-L-Glu or a pharmaceutically acceptable salt thereof.

58. The method of claim 23, wherein the peptide is L-Val-L-Thr or a pharmaceutically acceptable salt thereof.

59. The method of claim 33, wherein the peptide is L-Gly-L-Glu or a pharmaceutically acceptable salt thereof.

60. The method of claim 33, wherein the peptide is L-Val-L-Thr or a pharmaceutically acceptable salt thereof.

61. The method of claim 46, wherein the peptide is L-Gly-L-Glu or a pharmaceutically acceptable salt thereof.

62. The method of claim 46, wherein the peptide is L-Val-L-Thr or a pharmaceutically acceptable salt thereof.

63. The method of claim 52, wherein the peptide is L-Gly-L-Glu or a pharmaceutically acceptable salt thereof.

64. The method of claim 52, wherein the peptide is L-Val-L-Thr or a pharmaceutically acceptable salt thereof.

65. The method of claim 51, wherein said peptide having a potassium channel opener activity comprises two amino acid residues.

66. The kit of claim 6, wherein the peptide is L-Gly-L-Glu or a pharmaceutically acceptable salt thereof.

67. The kit of claim 6, wherein the peptide is L-Val-L-Thr or a pharmaceutically acceptable salt thereof.

* * * * *